(12) United States Patent
Coburn et al.

(10) Patent No.: US 8,497,383 B2
(45) Date of Patent: Jul. 30, 2013

(54) HIV PROTEASE INHIBITORS

(75) Inventors: Craig A. Coburn, Royersford, PA (US); M. Katharine Holloway, Lansdale, PA (US); Joseph P. Vacca, Telford, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/322,184

(22) PCT Filed: May 18, 2010

(86) PCT No.: PCT/US2010/035200
§ 371 (c)(1),
(2), (4) Date: Nov. 23, 2011

(87) PCT Pub. No.: WO2010/138338
PCT Pub. Date: Dec. 2, 2010

(65) Prior Publication Data
US 2012/0142752 A1   Jun. 7, 2012

Related U.S. Application Data

(60) Provisional application No. 61/181,406, filed on May 27, 2009.

(51) Int. Cl.
*C07D 207/14* (2006.01)
*A61K 31/40* (2006.01)

(52) U.S. Cl.
USPC .......................................... 548/557; 514/426

(58) Field of Classification Search
USPC .......................................... 548/557; 514/426
See application file for complete search history.

(56) References Cited

FOREIGN PATENT DOCUMENTS
WO    2009042093 A1    4/2009

OTHER PUBLICATIONS

Blum et al. (J. Med. Chem., 2008, 51, 2078-87).*
Specker, et al., Unexpected novel binding mode of pyrrolidine-based aspartyl protease inhibitors: design, sunthesis and crystal structure in complex with HIV protease. Chem Med. Chem. Jan. 2006, vol. 1, No. 1, pp. 106-117; p. 107, right col., para 2, p. 109, p. 110, left col. para 5, Table 2.
Blum, et al., Structure-guided design of C2-symmetric HIV-1 protease inhibitors based on a pyrrolidine scaffold. J. Med . Chem, Apr. 10, 2008, vol. 51, No. 7, pp. 2078-2087.

\* cited by examiner

*Primary Examiner* — Robert Havlin
(74) *Attorney, Agent, or Firm* — Sheldon O. Heber; Raynard Yuro

(57) ABSTRACT

Compounds of Formula (I) are disclosed; wherein $X^A$, k, A, B, $R^{3A}$, $R^{3B}$, $R^4$ and $R^5$ are defined herein. The compounds of Formula (I) are HIV protease inhibitors. The compounds and their pharmaceutically acceptable salts are useful for the prophylaxis or treatment of infection by HIV and the prophylaxis, treatment, or delay in the onset of AIDS. The compounds and their salts can be employed as ingredients in pharmaceutical compositions, optionally in combination with other antivirals, immunomodulators, antibiotics or vaccines.

(I)

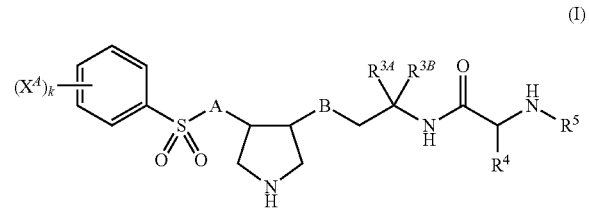

13 Claims, No Drawings

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Chemically Synthesized
<221> NAME/KEY: MOD_RES
<222> LOCATION: (5)...(5)
<223> OTHER INFORMATION: Xaa = betanapthyl alanine

<400> SEQUENCE: 1

Val Ser Gln Asn Xaa Pro Ile Val
1               5
```

HIV PROTEASE INHIBITORS

A Sequence Listing in the ASCII text file named MRLIFD00017USPCTSEQTXT.txt, created on Nov. 22, 2011, which is 537 bytes, is hereby incorporated by reference.

FIELD OF THE INVENTION

The present invention is directed to certain 3,4-disubstituted pyrrolidine compounds and their pharmaceutically acceptable salts. The compounds are HIV protease inhibitors and are useful for the prophylaxis of HIV infection and HIV replication, the treatment of HIV infection and HIV replication, the prophylaxis of AIDS, the treatment of AIDS, and the delay in the onset and/or progression of AIDS.

BACKGROUND OF THE INVENTION

A retrovirus designated human immunodeficiency virus (HIV), particularly the strains known as HIV type-1 (HIV-1) virus and type-2 (HIV-2) virus, is the etiological agent of acquired immunodeficiency syndrome (AIDS), a disease characterized by the destruction of the immune system, particularly of CD4 T-cells, with attendant susceptibility to opportunistic infections, and its precursor AIDS-related complex ("ARC"), a syndrome characterized by symptoms such as persistent generalized lymphadenopathy, fever and weight loss. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl et al., *Proc. Nat'l Acad. Sci.* 1988, 85: 4686, demonstrated that genetic inactivation of the HIV encoded protease resulted in the production of immature, non-infectious virus particles. These results indicated that inhibition of the HIV protease represents a viable method for the treatment of AIDS and the prevention or treatment of infection by HIV.

Nucleotide sequencing of HIV shows the presence of a pol gene in one open reading frame [Ratner et al., *Nature* 1985, 313: 277]. Amino acid sequence homology provides evidence that the pol sequence encodes reverse transcriptase, an endonuclease, HIV protease and gag, which encodes the core proteins of the virion (Toh et al., *EMBO J.* 1985, 4: 1267; Power et al., *Science* 1986, 231: 1567; Pearl et al., *Nature* 1987, 329: 351].

Several HIV protease inhibitors are presently approved for clinical use in the treatment of AIDS and HIV infection, including indinavir (see U.S. Pat. No. 5,413,999), amprenavir (U.S. Pat. No. 5,585,397), saquinavir (U.S. Pat. No. 5,196,438), ritonavir (U.S. Pat. No. 5,484,801), nelfinavir (U.S. Pat. No. 5,484,926), and atazanavir (U.S. Pat. No. 5,849,911 and U.S. Pat. No. 6,087,383). Each of these protease inhibitors is a peptide-derived peptidomimetic, competitive inhibitor of the viral protease which prevents cleavage of the HIV gag-pol polyprotein precursor. Tipranavir (U.S. Pat. No. 5,852,195) is a non-peptide peptidomimetic protease inhibitors also approved for use in treating HIV infection. The protease inhibitors are administered in combination with at least one and typically at least two other HIV antiviral agents, particularly nucleoside reverse transcriptase inhibitors such as zidovudine (AZT) and lamivudine (3TC) and/or non-nucleoside reverse transcriptase inhibitors such as efavirenz and nevirapine. Indinavir, for example, has been found to be highly effective in reducing HIV viral loads and increasing CD4 cell counts in HIV-infected patients, when used in combination with nucleoside reverse transcriptase inhibitors. See, for example, Hammer et al., *New England J. Med.* 1997, 337: 725-733 and Gulick et al., *New England J. Med.* 1997, 337: 734-739.

The established therapies employing a protease inhibitor are not suitable for use in all HIV-infected subjects. Some subjects, for example, cannot tolerate these therapies due to adverse effects. Many HIV-infected subjects often develop resistance to particular protease inhibitors. Accordingly, there is a continuing need for new compounds which are capable of inhibiting HIV protease and suitable for use in the treatment or prophylaxis of infection by HIV and/or for the treatment or prophylaxis or delay in the onset or progression of AIDS.

Of interest as background are the following references which disclose amino acid derivatives with HIV aspartyl protease inhibiting properties, processes for preparing the derivatives, and/or therapeutic uses of the derivatives: WO 01/68593, WO 02/064551 A1, WO 03/074467 A2, WO 2004/056764 A1, WO 2006/012725 A1, WO 2006/114001 A1, WO 2007/062526 A1, WO 2008/023273 A2, WO 2008/078200 A2, and U.S. Pat. No. 7,388,008 B2.

Also of interest is WO 2009/042093 which discloses certain lysine sulfonamide derivatives some of which are HIV protease inhibitors and others of which can be metabolized in vivo to HIV protease inhibitors. Many of the derivatives are characterized by the inclusion of branching on the lysine side chain.

SUMMARY OF THE INVENTION

The present invention is directed to certain 3,4-disubstituted pyrrolidine compounds and their use in the inhibition of HIV protease, the prophylaxis of infection by HIV, the treatment of infection by HIV, and the prophylaxis, treatment, and delay in the onset or progression of AIDS. More particularly, the present invention includes compounds of Formula I:

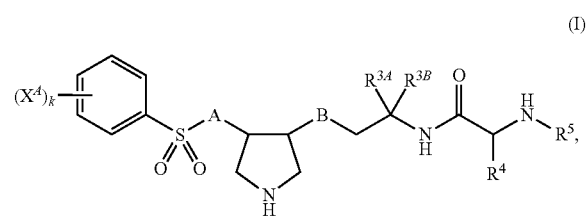

and pharmaceutically acceptable salts thereof, wherein:
A is N—$R^1$, or CH—$R^1$;
B is N—$R^2$ or CH—$R^2$;
$R^1$ is H, $C_{1-6}$ alkyl, $C_{1-6}$ fluoroalkyl, $C_{3-6}$ cycloalkyl, $C_{1-6}$ alkyl substituted with $C_{3-6}$ cycloalkyl; or $C_{1-6}$ alkyl substituted with AryA;
$R^2$ is H, $C_{1-6}$ alkyl, $C_{1-6}$ fluoroalkyl, $C_{3-6}$ cycloalkyl, $C_{1-6}$ alkyl substituted with $C_{3-6}$ cycloalkyl, $C_{1-6}$ alkyl substituted with AryB, C(O)—$C_{1-6}$ alkyl, or $SO_2$—$C_{1-6}$ alkyl;
$R^{3A}$ is H, $C_{1-6}$ alkyl, $C_{1-6}$ fluoroalkyl, $C_{3-5}$ cycloalkyl, or $C_{1-6}$ alkyl substituted with $C_{3-5}$ cycloalkyl;
$R^{3B}$ is H or $C_{1-6}$ alkyl;
each $X^A$ is independently:
(1) $C_{1-6}$ alkyl,
(2) $C_{3-6}$ cycloalkyl,
(3) $C_{1-6}$ haloalkyl,
(4) OH,
(5) O—$C_{1-6}$ alkyl, (6) O—$C_{1-6}$ haloalkyl,
(7) O—$C_{3-6}$ cycloalkyl,
(8) SH,
(9) S—$C_{1-6}$ alkyl,
(10) S—$C_{1-6}$ haloalkyl,
(11) S—$C_{3-6}$ cycloalkyl,
(12) halo,
(13) CN,
(14) $NO_2$,
(15) $NH_2$,
(16) N(H)—$C_{1-6}$ alkyl,
(17) N(—$C_{1-6}$ alkyl)$_2$,
(18) N(H)C(O)—$C_{1-6}$ alkyl,
(19) N(H)CH(O),
(20) CH(O),
(21) C(O)—$C_{1-6}$ alkyl,
(22) C(O)OH,
(23) C(O)O—$C_{1-6}$ alkyl,
(24) $SO_2H$,
(25) $SO_2$—$C_{1-6}$ alkyl, or
(26) $C_{1-6}$ alkyl substituted with
  (a) $C_{3-6}$ cycloalkyl,
  (b) $C_{1-6}$ haloalkyl,
  (c) OH,
  (d) O—$C_{1-6}$ alkyl,
  (e) O—$C_{1-6}$ haloalkyl,
  (f) O—$C_{3-6}$ cycloalkyl,
  (g) SH,
  (h) S—$C_{1-6}$ alkyl,
  (i) S—$C_{1-6}$ haloalkyl,
  (j) S—$C_{3-6}$ cycloalkyl,
  (k) halo,
  (l) CN,
  (m) $NO_2$,
  (n) $NH_2$,
  (o) N(H)—$C_{1-6}$ alkyl,
  (p) N(—$C_{1-6}$ alkyl)$_2$,
  (q) N(H)C(O)—$C_{1-6}$ alkyl,
  (r) N(H)CH(O),
  (s) CH(O),
  (t) C(O)—$C_{1-6}$ alkyl,
  (u) C(O)OH,
  (v) C(O)O—$C_{1-6}$ alkyl,
  (w) $SO_2H$, or
  (x) $SO_2$—$C_{1-6}$ alkyl;

or, alternatively, when two or more $X^A$ substituents are present on the phenyl ring and two of the $X^A$ are attached to adjacent carbon atoms of the phenyl ring, the two $X^A$ are optionally taken together with the carbon atoms to which they are attached to form a 5- or 6-membered, saturated or unsaturated heterocycle fused to the phenyl ring, wherein the heterocycle contains from 1 to 2 heteroatoms independently selected from N, O and S;

k is an integer equal to 0, 1, 2, or 3;

$R^4$ is:

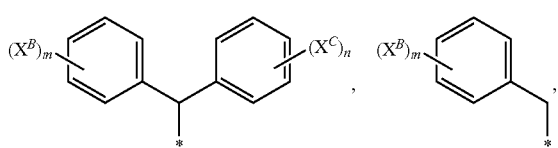

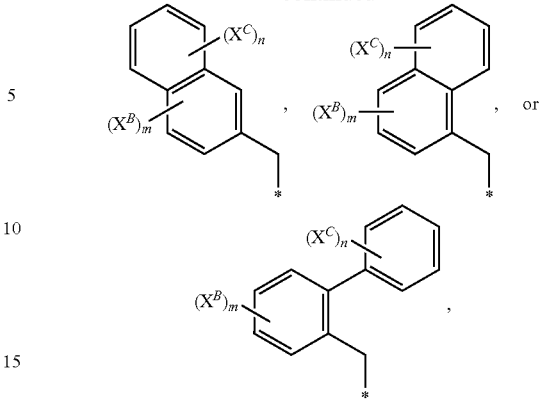

wherein the asterisk (*) denotes the point of attachment to the rest of the compound;

each $X^B$ and each $X^C$ are independently selected from the group consisting of
(1) $C_{1-6}$ alkyl,
(2) $C_{3-6}$ cycloalkyl,
(3) $C_{1-6}$ haloalkyl,
(4) OH,
(5) O—$C_{1-6}$ alkyl,
(6) O—$C_{1-6}$ haloalkyl,
(7) O—$C_{3-6}$ cycloalkyl,
(8) SH,
(9) S—$C_{1-6}$ alkyl,
(10) S—$C_{1-6}$ haloalkyl,
(11) S—$C_{3-6}$ cycloalkyl,
(12) halo,
(13) CN,
(14) $NO_2$,
(15) $NH_2$,
(16) N(H)—$C_{1-6}$ alkyl,
(17) N(—$C_{1-6}$ alkyl)$_2$,
(18) N(H)C(O)—$C_{1-6}$ alkyl,
(19) N(H)CH(O),
(20) CH(O),
(21) C(O)—$C_{1-6}$ alkyl,
(22) C(O)OH,
(23) C(O)O—$C_{1-6}$ alkyl,
(24) $SO_2H$,
(25) $SO_2$—$C_{1-6}$ alkyl; and
(26) $C_{1-6}$ alkyl substituted with:
  (a) $C_{1-6}$ haloalkyl,
  (b) OH
  (c) O—$C_{1-6}$ alkyl,
  (d) O—$C_{1-6}$ haloalkyl,
  (e) O—$C_{3-6}$ cycloalkyl,
  (f) SH,
  (g) S—$C_{1-6}$ alkyl,
  (h) halo,
  (i) CN,
  (j) $NO_2$,
  (k) $NH_2$,
  (l) N(H)—$C_{1-6}$ alkyl,
  (m) N(—$C_{1-6}$ alkyl)$_2$,
  (n) C(O)—$C_{1-6}$ alkyl,
  (o) C(O)OH,
  (p) C(O)O—$C_{1-6}$ alkyl, or
  (q) $SO_2$—$C_{1-6}$ alkyl;

m is an integer equal to 0, 1, 2, or 3;

n is an integer equal to 0, 1, 2, or 3;

$R^5$ is H, $C_{1-6}$ alkyl, $C_{3-6}$ cycloalkyl, $C_{1-6}$ alkyl substituted with $C_{3-6}$ cycloalkyl, or C(O)—$R^K$;

$R^K$ is:
(1) $C_{1-6}$ alkyl,
(2) $C_{3-6}$ cycloalkyl,
(3) $C_{1-6}$ alkyl substituted with $C_{3-6}$ cycloalkyl,
(4) O—$C_{1-6}$ alkyl,
(5) O—$C_{1-6}$ alkyl substituted with O—$C_{1-6}$ alkyl,
(6) O—$C_{1-6}$ fluoroalkyl,
(7) C(O)O—$C_{1-6}$ alkyl,
(8) $C_{1-6}$ alkyl substituted with C(O)O—$C_{1-6}$ alkyl,
(9) $C_{1-6}$ alkyl substituted with C(O)OH,
(10) $C_{1-6}$ alkyl substituted with C(O)—$C_{1-6}$ alkyl,
(11) N(H)—$C_{1-6}$ alkyl,
(12) N(—$C_{1-6}$ alkyl)$_2$,
(13) $C_{1-6}$ alkyl substituted with NH$_2$, N(H)—$C_{1-6}$ alkyl, or N(—$C_{1-6}$ alkyl)$_2$,
(14) AryC,
(15) $C_{1-6}$ alkyl substituted with AryC,
(16) O—$C_{1-6}$ alkyl substituted with AryC,
(17) HetA,
(18) $C_{1-6}$ alkyl substituted with HetA,
(19) O—$C_{1-6}$ alkyl substituted with HetA,
(20) HetB, or
(21) O-HetB;

AryA is an aryl which is independently phenyl or naphthyl, wherein the phenyl or naphthyl is optionally substituted with from 1 to 4 $Y^A$ wherein each $Y^A$ independently has the same definition as $X^B$;

AryB is an aryl which is independently phenyl or naphthyl, wherein the phenyl or naphthyl is optionally substituted with from 1 to 4 $Y^A$ wherein each $Y^A$ independently has the same definition as $X^B$;

AryC is an aryl which is independently phenyl or naphthyl, wherein the phenyl or naphthyl is optionally substituted with from 1 to 4 $Y^B$ wherein each $Y^B$ independently has the same definition as $X^B$;

HetA is a heteroaryl which is independently (i) a 5- or 6-membered heteroaromatic ring containing from 1 to 4 heteroatoms independently selected from N, O and S, or (ii) is a heterobicyclic ring selected from quinolinyl, isoquinolinyl, and quinoxalinyl; wherein the heteroaromatic ring (i) or the bicyclic ring (ii) is optionally substituted with from 1 to 4 $Y^C$ wherein each $Y^C$ independently has the same definition as $X^B$; and HetB is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or S(O)$_2$, and wherein the saturated or unsaturated heterocyclic ring is optionally substituted with from 1 to 4 substituents each of which is independently halogen, CN, $C_{1-6}$ alkyl, OH, oxo, O—$C_{1-6}$ alkyl, $C_{1-6}$ haloalkyl, O—$C_{1-6}$ haloalkyl, C(O)NH$_2$, C(O)N(H)—$C_{1-6}$ alkyl, C(O)N(—$C_{1-6}$ alkyl)$_2$, C(O)H, C(O)—$C_{1-6}$ alkyl, CO$_2$H, CO$_2$—$C_{1-6}$ alkyl, SO$_2$H, or SO$_2$—$C_{1-6}$ alkyl.

The present invention also includes pharmaceutical compositions containing a compound of Formula I or a pharmaceutically acceptable salt thereof. The present invention further includes methods involving compounds of Formula I for the treatment of AIDS, the delay in the onset or progression of AIDS, the prophylaxis of AIDS, the prophylaxis of infection by HIV, and the treatment of infection by HIV.

Other embodiments, sub-embodiments, aspects, classes, sub-classes and features of the present invention are either further described in or will be apparent from the ensuing description, examples and appended claims.

DETAILED DESCRIPTION OF THE INVENTION

The present invention includes compounds of Formula I above and pharmaceutically acceptable salts thereof. The compounds encompassed by Formula I are HIV protease inhibitors.

A first embodiment of the present invention (alternatively referred to herein as "Embodiment E1") is a compound of Formula I (alternatively and more simply referred to as "Compound I"), or a pharmaceutically acceptable salt thereof, wherein $R^1$ is $C_{1-6}$ alkyl or $C_{1-6}$ alkyl substituted with AryA; and all other variables are as originally defined (i.e., as defined for Compound I in the Summary of the Invention).

A second embodiment of the present invention (Embodiment E2) is a compound of Formula I, or a pharmaceutically acceptable salt thereof, wherein $R^1$ is $C_{3-6}$ branched alkyl or CH$_2$-AryA; and all other variables are as originally defined.

A third embodiment of the present invention (Embodiment E3) is a compound of Formula I, or a pharmaceutically acceptable salt thereof, wherein $R^1$ is CH(CH$_3$)$_2$, CH$_2$CH(CH$_3$)$_2$, CH$_2$CH$_2$CH(CH$_3$)$_2$, CH$_2$CH$_2$CH$_2$CH(CH$_3$)$_2$, or benzyl; and all other variables are as originally defined.

A fourth embodiment of the present invention (Embodiment E4) is a compound of Formula I, or a pharmaceutically acceptable salt thereof, wherein $R^1$ is $C_{1-6}$ alkyl; and all other variables are as originally defined.

A fifth embodiment of the present invention (Embodiment E5) is a compound of Formula I, or a pharmaceutically acceptable salt thereof, wherein $R^1$ is CH$_3$, CH$_2$CH$_3$, CH(CH$_3$)$_2$, CH$_2$CH$_2$CH$_3$, CH$_2$CH(CH$_3$)$_2$, CH$_2$CH$_2$CH(CH$_3$)$_2$, or CH$_2$CH$_2$CH$_2$CH(CH$_3$)$_2$; and all other variables are as originally defined.

A sixth embodiment of the present invention (Embodiment E6) is a compound of Formula I, or a pharmaceutically acceptable salt thereof, wherein $R^1$ is $C_{3-6}$ branched alkyl; and all other variables are as originally defined.

A seventh embodiment of the present invention (Embodiment E7) is a compound of Formula I, or a pharmaceutically acceptable salt thereof, wherein $R^1$ is CH(CH$_3$)$_2$, CH$_2$CH(CH$_3$)$_2$, CH$_2$CH$_2$CH(CH$_3$)$_2$, or CH$_2$CH$_2$CH$_2$CH(CH$_3$)$_2$; and all other variables are as originally defined.

An eighth embodiment of the present invention (Embodiment E8) is a compound of Formula I, or a pharmaceutically acceptable salt thereof, wherein $R^2$ is H, $C_{1-6}$ alkyl, $C_{1-6}$ alkyl substituted with AryB, C(O)—$C_{1-6}$ alkyl, or SO$_2$—$C_{1-6}$ alkyl; and all other variables are as originally defined or as defined in any of the preceding embodiments.

A ninth embodiment of the present invention (Embodiment E9) is a compound of Formula I, or a pharmaceutically acceptable salt thereof, wherein $R^2$ is H, $C_{1-4}$ alkyl, CH$_2$-AryB, C(O)—$C_{1-4}$ alkyl, or SO$_2$—$C_{1-4}$ alkyl; and all other variables are as originally defined or as defined in any of the preceding embodiments.

A tenth embodiment of the present invention (Embodiment E10) is a compound of Formula I, or a pharmaceutically acceptable salt thereof, wherein $R^2$ is H or $C_{1-6}$ alkyl; and all other variables are as originally defined or as defined in any of the preceding embodiments.

An eleventh embodiment of the present invention (Embodiment E11) is a compound of Formula I, or a pharmaceutically acceptable salt thereof, wherein $R^2$ is H or $C_{1-4}$ alkyl; and all other variables are as originally defined or as defined in any of the preceding embodiments.

A twelfth embodiment of the present invention (Embodiment E12) is a compound of Formula I, or a pharmaceutically acceptable salt thereof, wherein $R^2$ is H or $CH_3$; and all other variables are as originally defined or as defined in any of the preceding embodiments.

A thirteenth embodiment of the present invention (Embodiment E13) is a compound of Formula I, or a pharmaceutically acceptable salt thereof, wherein A is N—$R^1$; B is N—$R^2$; and all other variables are as originally defined or as defined in any of the preceding embodiments.

A fourteenth embodiment of the present invention (Embodiment E14) is a compound of Formula I, or a pharmaceutically acceptable salt thereof, wherein A is N—$R^1$; B is CH—$R^2$; and all other variables are as originally defined or as defined in any of the preceding embodiments.

A fifteenth embodiment of the present invention (Embodiment E15) is a compound of Formula I, or a pharmaceutically acceptable salt thereof, wherein A is CH—$R^1$; B is N—$R^2$; and all other variables are as originally defined or as defined in any of the preceding embodiments.

A sixteenth embodiment of the present invention (Embodiment E16) is a compound of Formula I, or a pharmaceutically acceptable salt thereof, wherein $R^{3A}$ is H or $C_{1-6}$ alkyl; and all other variables are as originally defined or as defined in any of the preceding embodiments.

A seventeenth embodiment of the present invention (Embodiment E17) is a compound of Formula I, or a pharmaceutically acceptable salt thereof, wherein $R^{3A}$ is H or $C_{1-4}$ alkyl; $R^{3B}$ is H or $C_{1-4}$ alkyl; and all other variables are as originally defined or as defined in any of the preceding embodiments.

An eighteenth embodiment of the present invention (Embodiment E18) is a compound of Formula I, or a pharmaceutically acceptable salt thereof, wherein $R^{3A}$ is H, $CH_3$, $CH_2CH_3$, $CH(CH_3)_2$, $CH_2CH_2CH_3$, $CH_2CH(CH_3)_2$, $C(CH_3)_3$, $CH_2CH_2CH(CH_3)_2$, or $CH_2CH_2CH_2CH(CH_3)_2$; $R^{3A}$ is H or $CH_3$; and all other variables are as originally defined or as defined in any of the preceding embodiments.

A nineteenth embodiment of the present invention (Embodiment E19) is a compound of Formula I, or a pharmaceutically acceptable salt thereof, wherein either (i) $R^{3A}$ is H, $CH_3$, $CH_2CH_3$, $CH(CH_3)_2$, $CH_2CH_2CH_3$, $CH_2CH(CH_3)_2$, $C(CH_3)_3$, $CH_2CH_2CH(CH_3)_2$, or $CH_2CH_2CH_2CH(CH_3)_2$, and $R^{3B}$ is H; or (ii) $R^{3A}$ and $R^{3B}$ are both $CH_3$; and all other variables are as originally defined or as defined in any of the preceding embodiments.

A twentieth embodiment of the present invention (Embodiment E20) is a compound of Formula I, or a pharmaceutically acceptable salt thereof, wherein $R^4$ is:

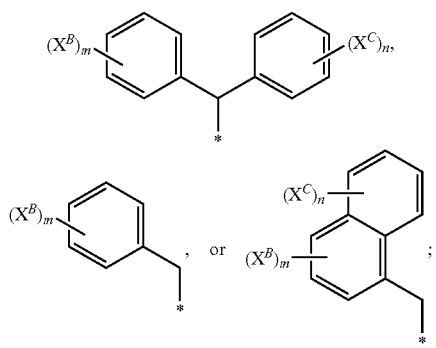

and all other variables are as originally defined or as defined in any of the preceding embodiments.

A twenty-first embodiment of the present invention (Embodiment E21) is a compound of Formula I, or a pharmaceutically acceptable salt thereof, wherein $R^4$ is:

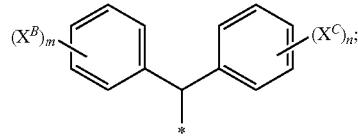

and all other variables are as originally defined or as defined in any of the preceding embodiments.

A twenty-second embodiment of the present invention (Embodiment E22) is a compound of Formula I, or a pharmaceutically acceptable salt thereof, wherein $R^4$ is:

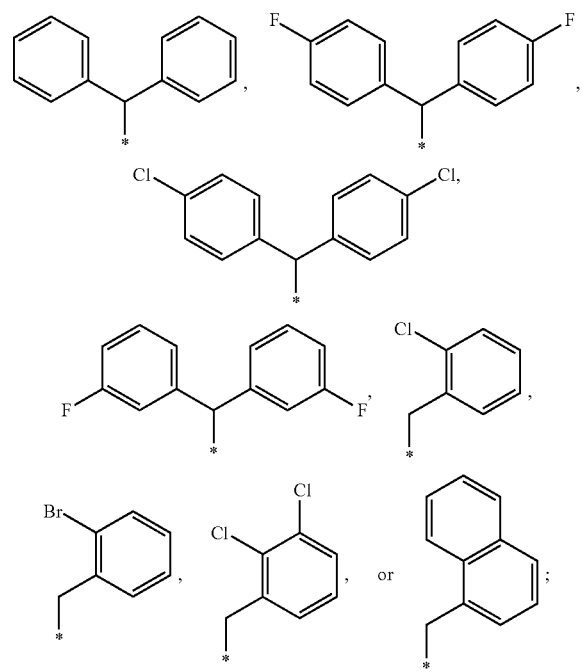

and all other variables are as originally defined or as defined in any of the preceding embodiments.

A twenty-third embodiment of the present invention (Embodiment E23) is a compound of Formula I, or a pharmaceutically acceptable salt thereof, wherein $R^4$ is:

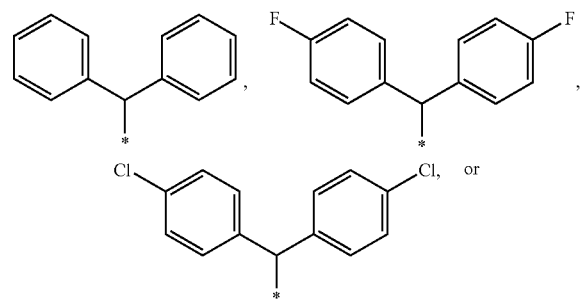

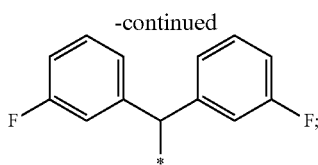

and all other variables are as originally defined or as defined in any of the preceding embodiments. In an aspect of this embodiment, $R^4$ is

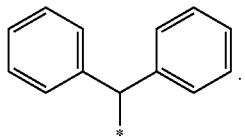

A twenty-fourth embodiment of the present invention (Embodiment E24) is a compound of Formula I, or a pharmaceutically acceptable salt thereof, wherein $R^5$ is H, $C_{1-6}$ alkyl, C(O)—$C_{1-6}$ alkyl, C(O)O—$C_{1-6}$ alkyl, C(O)N(—$C_{1-6}$ alkyl)$_2$, C(O)—HetA, C(O)OCH$_2$—HetA, C(O)—HetB, or C(O)O-HetB; and all other variables are as originally defined or as defined in any of the preceding embodiments.

A twenty-fifth embodiment of the present invention (Embodiment E25) is a compound of Formula I, or a pharmaceutically acceptable salt thereof, wherein $R^5$ is H, CH$_3$, C(O)CH$_3$, C(O)OCH$_3$, C(O)OC(CH$_3$)$_3$, C(O)N(CH$_3$)$_2$, C(O)-morpholinyl, C(O)-pyridyl, or C(O)O—CH$_2$-pyridyl; and all other variables are as originally defined or as defined in any of the preceding embodiments.

A twenty-sixth embodiment of the present invention (Embodiment E26) is a compound of Formula I, or a pharmaceutically acceptable salt thereof, wherein $R^5$ is H, CH$_3$, C(O)OCH$_3$, C(O)OC(CH$_3$)$_3$, or C(O)O—CH$_2$-pyridyl; and all other variables are as originally defined or as defined in any of the preceding embodiments.

A twenty-seventh embodiment of the present invention (Embodiment E27) is a compound of Formula I, or a pharmaceutically acceptable salt thereof, wherein $R^5$ is C(O)O—$C_{1-6}$ alkyl; and all other variables are as originally defined or as defined in any of the preceding embodiments.

A twenty-eighth embodiment of the present invention (Embodiment E28) is a compound of Formula I, or a pharmaceutically acceptable salt thereof, wherein $R^5$ is C(O)OCH$_3$ or C(O)OC(CH$_3$)$_3$; and all other variables are as originally defined or as defined in any of the preceding embodiments.

A twenty-ninth embodiment of the present invention (Embodiment E29) is a compound of Formula I, or a pharmaceutically acceptable salt thereof, wherein $R^5$ is C(O)OCH$_3$; and all other variables are as originally defined or as defined in any of the preceding embodiments.

A thirtieth embodiment of the present invention (Embodiment E30) is a compound of Formula I, or a pharmaceutically acceptable salt thereof, wherein each $X^A$ is independently:
(1) $C_{1-3}$ alkyl,
(2) cyclopropyl,
(3) CF$_3$,
(4) OH,
(5) O—$C_{1-3}$ alkyl,
(6) OCF$_3$,
(7) Cl,
(8) Br,
(9) F,
(10) CN,
(11) NO$_2$,
(12) NH$_2$,
(13) N(H)—$C_{1-3}$ alkyl,
(14) N(—$C_{1-3}$ alkyl)$_2$,
(15) C(O)—$C_{1-3}$ alkyl,
(16) CO$_2$H,
(17) C(O)O—$C_{1-3}$ alkyl, or
(18) $C_{1-3}$ alkyl substituted with
(a) cyclopropyl,
(b) CF$_3$,
(c) OH,
(d) O—$C_{1-3}$ alkyl,
(e) OCF$_3$,
(f) Cl,
(g) Br,
(h) F,
(i) CN,
(j) NO$_2$,
(k) NH$_2$,
(l) N(H)—$C_{1-3}$ alkyl,
(m) N(—$C_{1-3}$ alkyl)$_2$,
(n) C(O)—$C_{1-3}$ alkyl,
(o) CO$_2$H, or
(p) C(O)O—$C_{1-3}$ alkyl;
or, alternatively, when two $X^A$ substituents are present on the phenyl ring and the two $X^A$ are attached to adjacent carbon atoms of the phenyl ring, the two $X^A$ are optionally taken together with the carbon atoms to which they are attached to form a 5- or 6-membered, saturated or unsaturated heterocycle fused to the phenyl ring, wherein the heterocycle contains from 1 to 2 heteroatoms independently selected from N, O and S (e.g., the two $X^A$ are optionally taken together with the carbon atoms to which they are attached to form —OCH$_2$O— or —OCH$_2$CH$_2$O—); k is an integer equal to 0, 1 or 2; and all other variables are as originally defined or as defined in any of the preceding embodiments.

A thirty-first embodiment of the present invention (Embodiment E31) is a compound of Formula I, or a pharmaceutically acceptable salt thereof, wherein each $X^A$ is independently:
(1) CH$_3$,
(2) CH$_2$CH$_3$,
(3) CF$_3$,
(4) OH,
(5) OCH$_3$,
(6) OCF$_3$,
(7) Cl,
(8) Br,
(9) F,
(10) CN,
(11) NH$_2$,
(12) N(H)CH$_3$,
(13) N(CH$_3$)$_2$,
(14) C(O)CH$_3$,
(15) C(O)OCH$_3$,
(16) CH$_2$OH,
(17) CH$_2$OCH$_3$,
(18) CH$_2$NH$_2$,
(19) CH$_2$N(H)CH$_3$,
(20) CH$_2$N(CH$_3$)$_2$,
(21) CH(CH$_3$)OH,
(22) CH(CH$_3$)OCH$_3$,
(23) CH(CH$_3$)NH$_2$,
(24) CH(CH$_3$)N(H)CH$_3$, or
(25) CH(CH$_3$)N(CH$_3$)$_2$;

or, alternatively, when two $X^A$ substituents are present on the phenyl ring and the two $X^A$ are attached to adjacent carbon atoms of the phenyl ring, the two $X^A$ are optionally taken together with the carbon atoms to which they are attached to form a 5- or 6-membered, saturated or unsaturated heterocycle fused to the phenyl ring, wherein the heterocycle contains from 1 to 2 heteroatoms independently selected from N, O and S (e.g., the two $X^A$ are optionally taken together with the carbon atoms to which they are attached to form —OCH$_2$O— or —OCH$_2$CH$_2$O—); k is an integer equal to 0, 1, or 2; and all other variables are as originally defined or as defined in any of the preceding embodiments.

A thirty-second embodiment of the present invention (Embodiment E32) is a compound of Formula I, or a pharmaceutically acceptable salt thereof, wherein there are 1 or 2 $X^A$ groups on the phenylsulfonyl moiety (i.e., k is 1 or 2) wherein one $X^A$ is in the para position on the phenyl ring and is CH$_3$, Cl, Br, F, NH$_2$, CH$_2$NH$_2$, C(O)CH$_3$, CH$_2$OH, or CH(CH$_3$)OH; and the other, optional $X^A$ is in the meta position on the phenyl ring and is Cl, Br, or F; or, alternatively, when two $X^A$ substituents are present on the phenyl ring (i.e., k is 2) and the two $X^A$ are attached to adjacent carbon atoms, the two $X^A$ are optionally taken together with the carbon atoms to which they are attached to form —OCH$_2$O— or —OCH$_2$CH$_2$O—; and all other variables are as originally defined or as defined in any of the preceding embodiments.

A thirty-third embodiment of the present invention (Embodiment E33) is a compound of Formula I, or a pharmaceutically acceptable salt thereof, wherein there is one $X^A$ group which is NH$_2$ in the para position of the phenyl ring; and all other variables are as originally defined or as defined in any of the preceding embodiments.

A thirty-fourth embodiment of the present invention (Embodiment E34) is a compound of Formula I, or a pharmaceutically acceptable salt thereof, wherein each $X^B$ and each $X^C$ are independently selected from the group consisting of:
  (1) $C_{1-3}$ alkyl,
  (2) cyclopropyl,
  (3) CF$_3$,
  (4) OH,
  (5) O—$C_{1-3}$ alkyl,
  (6) OCF$_3$,
  (7) Cl,
  (8) Br,
  (9) F,
  (10) CN,
  (11) NO$_2$,
  (12) NH$_2$,
  (13) N(H)—$C_{1-3}$ alkyl,
  (14) N(—$C_{1-3}$ alkyl)$_2$,
  (15) C(O)—$C_{1-3}$ alkyl,
  (16) CO$_2$H,
  (17) C(O)O—$C_{1-3}$ alkyl,
  (18) CH$_2$OH, and
  (19) CH$_2$O—$C_{1-3}$ alkyl;
m is an integer equal to 0, 1, or 2; n is an integer equal to 0, 1, or 2; and all other variables are as originally defined or as defined in any of the preceding embodiments.

A thirty-fifth embodiment of the present invention (Embodiment E35) is a compound of Formula I, or a pharmaceutically acceptable salt thereof, wherein each $X^B$ and each $X^C$ are independently selected from the group consisting of:
  (1) CH$_3$,
  (2) CH$_2$CH$_3$,
  (3) CF$_3$,
  (4) OH,
  (5) OCH$_3$,
  (6) OCF$_3$,
  (7) Cl,
  (8) Br,
  (9) F,
  (10) CN,
  (11) NH$_2$,
  (12) N(H)CH$_3$,
  (13) N(CH$_3$)$_2$,
  (14) C(O)CH$_3$,
  (15) C(O)OCH$_3$,
  (16) CH$_2$OH, and
  (17) CH$_2$OCH$_3$;
m is an integer equal to 0, 1, or 2; n is an integer equal to 0, 1, or 2; and all other variables are as originally defined or as defined in any of the preceding embodiments.

A thirty-sixth embodiment of the present invention (Embodiment E36) is a compound of Formula I, or a pharmaceutically acceptable salt thereof, wherein AryA is phenyl which is optionally substituted with from 1 to 3 substituents each of which is independently $C_{1-3}$ alkyl, CF$_3$, OH, O—$C_{1-3}$ alkyl, OCF$_3$, Cl, Br, F, CN, NH$_2$, N(H)—$C_{1-3}$ alkyl, N(—$C_{1-3}$ alkyl)$_2$, C(O)—$C_{1-3}$ alkyl, CO$_2$H, C(O)O—$C_{1-3}$ alkyl, CH$_2$OH, CH$_2$O—$C_{1-3}$ alkyl, C(O)—$C_{1-3}$ alkyl, or SO$_2$—$C_{1-3}$ alkyl; and all other variables are as originally defined or as defined in any of the preceding embodiments.

A thirty-seventh embodiment of the present invention (Embodiment E37) is a compound of Formula I, or a pharmaceutically acceptable salt thereof, wherein AryA is phenyl which is optionally substituted with from 1 to 3 substituents each of which is independently CH$_3$, CF$_3$, OH, OCH$_3$, OCF$_3$, Cl, Br, F, CN, NH$_2$, N(H)CH$_3$, N(CH$_3$)$_2$, C(O)CH$_3$, CO$_2$H, C(O)OCH$_3$, CH$_2$OH, CH$_2$OCH$_3$, C(O)CH$_3$, or SO$_2$CH$_3$; and all other variables are as originally defined or as defined in any of the preceding embodiments.

A thirty-eighth embodiment of the present invention (Embodiment E38) is a compound of Formula I, or a pharmaceutically acceptable salt thereof, wherein AryB is phenyl which is optionally substituted with from 1 to 3 substituents each of which is independently $C_{1-3}$ alkyl, CF$_3$, OH, O—$C_{1-3}$ alkyl, OCF$_3$, Cl, Br, F, CN, NH$_2$, N(H)—$C_{1-3}$ alkyl, N(—$C_{1-3}$ alkyl)$_2$, C(O)—$C_{1-3}$ alkyl, CO$_2$H, C(O)O—$C_{1-3}$ alkyl, CH$_2$OH, CH$_2$O—$C_{1-3}$ alkyl, C(O)—$C_{1-3}$ alkyl, or SO$_2$—$C_{1-3}$ alkyl; and all other variables are as originally defined or as defined in any of the preceding embodiments.

A thirty-ninth embodiment of the present invention (Embodiment E39) is a compound of Formula I, or a pharmaceutically acceptable salt thereof, wherein AryB is phenyl which is optionally substituted with from 1 to 3 substituents each of which is independently CH$_3$, CF$_3$, OH, OCH$_3$, OCF$_3$, Cl, Br, F, CN, NH$_2$, N(H)CH$_3$, N(CH$_3$)$_2$, C(O)CH$_3$, CO$_2$H, C(O)OCH$_3$, CH$_2$OH, CH$_2$OCH$_3$, C(O)CH$_3$, or SO$_2$CH$_3$; and all other variables are as originally defined or as defined in any of the preceding embodiments.

A fortieth embodiment of the present invention (Embodiment E40) is a compound of Formula I, or a pharmaceutically acceptable salt thereof, wherein AryC is phenyl which is optionally substituted with from 1 to 3 substituents each of which is independently $C_{1-3}$ alkyl, CF$_3$, OH, O—$C_{1-3}$ alkyl, OCF$_3$, Cl, Br, F, CN, NH$_2$, N(H)—$C_{1-3}$ alkyl, N(—$C_{1-3}$ alkyl)$_2$, C(O)—$C_{1-3}$ alkyl, CO$_2$H, C(O)O—$C_{1-3}$ alkyl, CH$_2$OH, CH$_2$O—$C_{1-3}$ alkyl, C(O)—$C_{1-3}$ alkyl, or SO$_2$—$C_{1-3}$ alkyl; and all other variables are as originally defined or as defined in any of the preceding embodiments.

A forty-first embodiment of the present invention (Embodiment E41) is a compound of Formula I, or a pharmaceutically acceptable salt thereof, wherein AryC is phenyl which is optionally substituted with from 1 to 3 substituents each of which is independently CH$_3$, CF$_3$, OH, OCH$_3$, OCF$_3$, Cl, Br, F, CN, NH$_2$, N(H)CH$_3$, N(CH$_3$)$_2$, C(O)CH$_3$, CO$_2$H, C(O)OCH$_3$, CH$_2$OH, CH$_2$OCH$_3$, C(O)CH$_3$, or SO$_2$CH$_3$; and all other variables are as originally defined or as defined in any of the preceding embodiments.

A forty-second embodiment of the present invention (Embodiment E42) is a compound of Formula I, or a pharmaceutically acceptable salt thereof, wherein HetA is a heteroaryl selected from the group consisting of pyrrolyl, imidazolyl, pyridyl, pyrazinyl, quinolyl, isoquinolyl, and quinoxalinyl, wherein the heteroaryl is optionally substituted with from 1 to 3 substituents each of which is independently C$_{1-3}$ alkyl, CF$_3$, OH, O—C$_{1-3}$ alkyl, OCF$_3$, Cl, Br, F, CN, NH$_2$, N(H)—C$_{1-3}$ alkyl, N(C$_{1-3}$ alkyl)$_2$, C(O)—C$_{1-3}$ alkyl, CO$_2$—C$_{1-3}$ alkyl, or SO$_2$—C$_{1-3}$ alkyl; and all other variables are as originally defined or as defined in any of the preceding embodiments.

A forty-third embodiment of the present invention (Embodiment E43) is a compound of Formula I, or a pharmaceutically acceptable salt thereof, wherein HetA is a heteroaryl selected from the group consisting of pyrrolyl, imidazolyl, pyridyl, pyrazinyl, quinolyl, isoquinolyl, and quinoxalinyl, wherein the heteroaryl is optionally substituted with from 1 to 3 substituents each of which is independently CH$_3$, CF$_3$, OH, OCH$_3$, OCF$_3$, Cl, Br, F, CN, NH$_2$, N(H)CH$_3$, N(CH$_3$)$_2$, C(O)CH$_3$, CO$_2$CH$_3$, or SO$_2$CH$_3$; and all other variables are as originally defined or as defined in any of the preceding embodiments.

A forty-fourth embodiment of the present invention (Embodiment E44) is a compound of Formula I, or a pharmaceutically acceptable salt thereof, wherein HetA is pyridyl; and all other variables are as originally defined or as defined in any of the preceding embodiments. In an aspect of this embodiment, HetA is 2-pyridyl. In another aspect of this embodiment, HetA is 3-pyridyl. In still another aspect of this embodiment, HetA is 4-pyridyl.

A forty-fifth embodiment of the present invention (Embodiment E45) is a compound of Formula I, or a pharmaceutically acceptable salt thereof, wherein HetB is a saturated heterocyclic ring selected from the group consisting of tetrahydrofuranyl, pyrrolidinyl, piperidinyl, piperazinyl, morpholinyl, and thiomorpholinyl in which the S is optionally oxidized to S(O) or S(O)$_2$, and wherein the ring is optionally substituted with 1 or 2 substituents each of which is independently C$_{1-3}$ alkyl, oxo, C(O)N(C$_{1-3}$ alkyl)$_2$, C(O)—C$_{1-3}$ alkyl, CO$_2$—C$_{1-3}$ alkyl, or S(O)$_2$—C$_{1-3}$ alkyl; and all other variables are as originally defined or as defined in any of the preceding embodiments.

A forty-sixth embodiment of the present invention (Embodiment E46) is a compound of Formula I, or a pharmaceutically acceptable salt thereof, wherein HetB is a saturated heterocyclic ring selected from the group consisting of tetrahydrofuranyl, pyrrolidinyl, piperidinyl, piperazinyl, morpholinyl, and thiomorpholinyl in which the S is optionally oxidized to S(O) or S(O)$_2$, and wherein the ring is optionally substituted with 1 or 2 substituents each of which is independently CH$_3$, oxo, C(O)N(CH$_3$)$_2$, C(O)CH$_3$, CO$_2$CH$_3$, or S(O)$_2$CH$_3$; and all other variables are as originally defined or as defined in any of the preceding embodiments.

A forty-seventh embodiment of the present invention (Embodiment E47) is a compound of Formula I, or a pharmaceutically acceptable salt thereof, wherein HetB is morpholinyl; and all other variables are as originally defined or as defined in any of the preceding embodiments. In an aspect of this embodiment, HetB is 4-morpholinyl.

A forty-eighth embodiment of the present invention (Embodiment E48) is a compound of Formula I, or a pharmaceutically acceptable salt thereof, wherein the compound is a compound of Formula II:

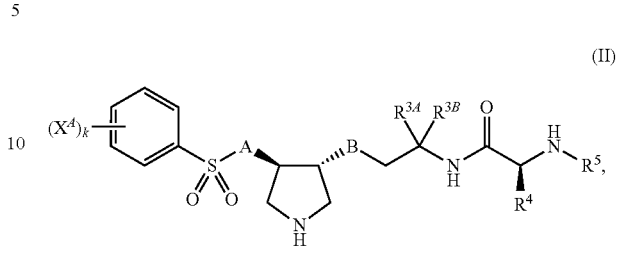

(II)

or a pharmaceutically acceptable salt thereof, wherein all of the variables are as originally defined. Sub-embodiments include Compound II, or a pharmaceutically acceptable salt thereof, incorporating one, two, three or more of the definitions of the variables $X^A$, k, A, B, $R^1$, $R^2$, $R^4$, $X^B$, $X^C$, m, n, $R^{3A}$, $R^{3B}$, $R^4$, $R^5$, AryA, AryB, AryC, HetA and HetB from the foregoing embodiments. Each such possible combination is a separate sub-embodiment. It is understood that certain combinations of the foregoing embodiments cannot be incorporated into the same sub-embodiment. For example, Embodiment E4 (i.e., $R^1$ is C$_{1-6}$ alkyl) cannot be combined with Embodiment E36 or Embodiment E37, both of which are directed to AryA, because AryA is a variable that appears only in certain definitions of $R^1$, but does not appear in the definition of $R^1$ in Embodiment E4. As another example, Embodiments E22 and E23 defining $R^4$ cannot be combined with Embodiments E34 and E35 directed to $X^B$ and $X^C$, because $X^B$ and $X^C$ appear only in certain definitions of $R^4$, but not in the definitions of $R^4$ in Embodiments E22 and E23.

A first class of compounds of the present invention (alternatively referred to herein as Class C1) includes compounds of Formula I and pharmaceutically acceptable salts thereof, wherein:
A is N—$R^1$ or CH—$R^1$;
B is N—$R^2$ or CH—$R^2$;
$R^1$ is C$_{1-6}$ alkyl or C$_{1-6}$ alkyl substituted with AryA;
$R^2$ is H, C$_{1-6}$ alkyl, C$_{1-6}$ alkyl substituted with AryB, C(O)—C$_{1-6}$ alkyl, or SO$_2$—C$_{1-6}$ alkyl;
$R^{3A}$ is H or C$_{1-6}$ alkyl;
$R^{3B}$ is H or C$_{1-6}$ alkyl;
$R^4$ is:

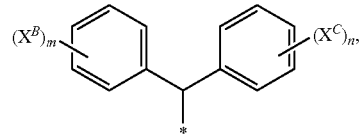

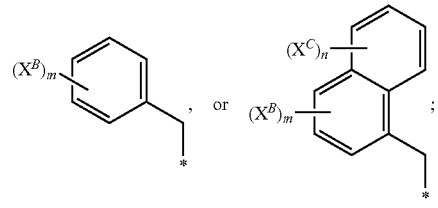

$X^B$, $X^C$, m and n are as defined in Embodiment E34;
$X^A$ and k are as defined in Embodiment E30;
$R^5$ is H, C$_{1-6}$ alkyl, C(O)—C$_{1-6}$ alkyl, C(O)O—C$_{1-6}$ alkyl, C(O)N(—C$_{1-6}$ alkyl)$_2$, C(O)—HetA, C(O)OCH$_2$—HetA, C(O)—HetB, or C(O)O-HetB;

AryA is phenyl which is optionally substituted with from 1 to 3 substituents each of which is independently $C_{1-3}$ alkyl, $CF_3$, OH, O—$C_{1-3}$ alkyl, $OCF_3$, Cl, Br, F, CN, $NH_2$, N(H)—$C_{1-3}$ alkyl, N(—$C_{1-3}$ alkyl)$_2$, C(O)—$C_{1-3}$ alkyl, $CO_2H$, C(O)O—$C_{1-3}$ alkyl, $CH_2OH$, $CH_2O$—$C_{1-3}$ alkyl, C(O)—$C_{1-3}$ alkyl, or $SO_2$—$C_{1-3}$ alkyl;

HetA is a heteroaryl selected from the group consisting of pyrrolyl, imidazolyl, pyridyl, pyrazinyl, quinolyl, isoquinolyl, and quinoxalinyl, wherein the heteroaryl is optionally substituted with from 1 to 3 substituents each of which is independently $C_{1-3}$ alkyl, $CF_3$, OH, O—$C_{1-3}$ alkyl, $OCF_3$, Cl, Br, F, CN, $NH_2$, N(H)—$C_{1-3}$ alkyl, N($C_{1-3}$ alkyl)$_2$, C(O)—$C_{1-3}$ alkyl, $CO_2$—$C_{1-3}$ alkyl, or $SO_2$—$C_{1-3}$ alkyl; and HetB is a saturated heterocyclic ring selected from the group consisting of tetrahydrofuranyl, pyrrolidinyl, piperidinyl, piperazinyl, morpholinyl, and thiomorpholinyl in which the S is optionally oxidized to S(O) or S(O)$_2$, and wherein the ring is optionally substituted with 1 or 2 substituents each of which is independently $C_{1-3}$ alkyl, oxo, C(O)N($C_{1-3}$ alkyl)$_2$, C(O)—$C_{1-3}$ alkyl, $CO_2$—$C_{1-3}$ alkyl, or $S(O)_2$—$C_{1-3}$ alkyl.

A first sub-class of the first class (alternatively referred to herein as "Sub-class C1-S1") includes compounds of Formula I and pharmaceutically acceptable salts thereof, wherein:

$R^1$ is $C_{3-6}$ branched alkyl or $CH_2$-AryA;
$R^2$ is H, $C_{1-4}$ alkyl, $CH_2$-AryB, C(O)—$C_{1-4}$ alkyl, or $SO_2$—$C_{1-4}$ alkyl;
$R^{3A}$ is H or $C_{1-4}$ alkyl;
$R^{3B}$ is H or $C_{1-4}$ alkyl;
$R^4$ is:

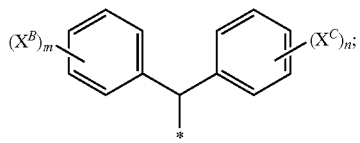

$R^5$ is C(O)O—$C_{1-6}$ alkyl;
and all other variables are as originally defined in Class C1.

A second sub-class of the first class (Sub-class C1-S2) includes compounds of Formula I and pharmaceutically acceptable salts thereof, wherein $R^1$ is $C_{3-6}$ branched alkyl; and all of the other variables are as defined in Sub-class C1-S1.

A second class of compounds of the present invention (Class C2) includes compounds of Formula I and pharmaceutically acceptable salts thereof, wherein:

A is N—$R^1$;
B is N—$R^2$;
$R^1$ is $C_{3-6}$ alkyl or $CH_2$-AryA;
$R^2$ is H or $C_{1-6}$ alkyl;
$R^{3A}$ is H or $C_{1-6}$ alkyl;
$R^{3B}$ is H or $C_{1-6}$ alkyl;
$R^4$ is:

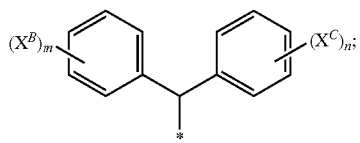

each $X^B$ and each $X^C$ are independently selected from the group consisting of: (1) $C_{1-3}$ alkyl, (2) cyclopropyl, (3) $CF_3$, (4) OH, (5) O—$C_{1-3}$ alkyl, (6) $OCF_3$, (7) Cl, (8) Br, (9) F, (10) CN, (11) $NO_2$, (12) $NH_2$, (13) N(H)—$C_{1-3}$ alkyl, (14) N(—$C_{1-3}$ alkyl)$_2$, (15) C(O)—$C_{1-3}$ alkyl, (16) $CO_2H$, (17) C(O)O—$C_{1-3}$ alkyl, (18) $CH_2OH$, and (19) $CH_2O$—$C_{1-3}$ alkyl;

m is an integer equal to 0, 1, or 2;
n is an integer equal to 0, 1, or 2;
each $X^A$ is independently: (1) $C_{1-3}$ alkyl, (2) cyclopropyl, (3) $CF_3$, (4) OH, (5) O—$C_{1-3}$ alkyl, (6) $OCF_3$, (7) Cl, (8) Br, (9) F, (10) CN, (11) $NO_2$, (12) $NH_2$, (13) N(H)—$C_{1-3}$ alkyl, (14) N(—$C_{1-3}$ alkyl)$_2$, (15) C(O)—$C_{1-3}$ alkyl, (16) $CO_2H$, (17) C(O)O—$C_{1-3}$ alkyl, or (18) $C_{1-3}$ alkyl substituted with (a) cyclopropyl, (b) $CF_3$, (c) OH, (d) O—$C_{1-3}$ alkyl, (e) $OCF_3$, (f) Cl, (g) Br, (h) F, (i) CN, (j) $NO_2$, (k) $NH_2$, (l) N(H)—$C_{1-3}$ alkyl, (m) N(—$C_{1-3}$ alkyl)$_2$, (n) C(O)—$C_{1-3}$ alkyl, (O)$CO_2H$, or (p) C(O)O—$C_{1-3}$ alkyl;

k is an integer equal to 0, 1, or 2;
or, alternatively, when two $X^A$ substituents are present on the phenyl ring and the two $X^A$ are attached to adjacent carbon atoms of the phenyl ring, the two $X^A$ are optionally taken together with the carbon atoms to which they are attached to form a 5- or 6-membered, saturated or unsaturated heterocycle fused to the phenyl ring, wherein the heterocycle contains from 1 to 2 heteroatoms independently selected from N, O and S;

$R^5$ is C(O)O—$C_{1-6}$ alkyl; and
AryA is phenyl which is optionally substituted with from 1 to 3 substituents each of which is independently $C_{1-3}$ alkyl, $CF_3$, OH, O—$C_{1-3}$ alkyl, $OCF_3$, Cl, Br, F, CN, $NH_2$, N(H)—$C_{1-3}$ alkyl, N(—$C_{1-3}$ alkyl)$_2$, C(O)—$C_{1-3}$ alkyl, $CO_2H$, C(O)O—$C_{1-3}$ alkyl, $CH_2OH$, $CH_2O$—$C_{1-3}$ alkyl, C(O)—$C_{1-3}$ alkyl, or $SO_2$—$C_{1-3}$ alkyl.

A first sub-class of the first class (Sub-class C2-S1) includes compounds of Formula I and pharmaceutically acceptable salts thereof, wherein $R^1$ is $C_{3-6}$ branched alkyl or $CH_2$-AryA; and all of the other variables are as defined in Class C2.

A second sub-class of the second class (Sub-class C2-S2) includes compounds of Formula I and pharmaceutically acceptable salts thereof, wherein $R^1$ is $C_{3-6}$ branched alkyl; and all of the other variables are as defined in Class C2.

A third sub-class of the second class (Sub-class C2-S3) includes compounds of Formula I and pharmaceutically acceptable salts thereof, wherein the compounds are of Formula III:

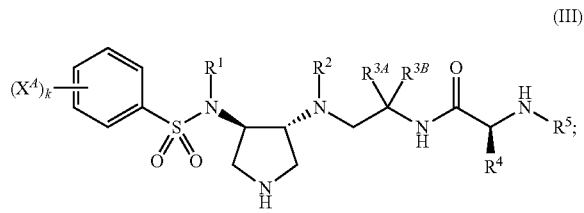

and all of the variables are as defined in Class C2. A subset of the sub-class includes compounds of Formula III and pharmaceutically acceptable salts thereof, wherein $R^1$ is $C_{3-6}$ branched alkyl or $CH_2$-AryA; and all of the other variables are as defined in Sub-class C2-S3. Another subset of the sub-class includes compounds of Formula III and pharmaceutically acceptable salts thereof, wherein $R^1$ is $C_{3-6}$ branched alkyl; and all of the other variables are as defined in Sub-class C2-S3.

A third class of compounds of the present invention (Class C3) includes compounds of Formula I and pharmaceutically acceptable salts thereof, wherein:

A is N—$R^1$;
B is N—$R^2$;
$R^1$ is $CH(CH_3)_2$, $CH_2CH_2CH_3$, $CH_2CH(CH_3)_2$, $CH_2CH_2CH(CH_3)_2$, $CH_2CH_2CH_2CH(CH_3)_2$, or benzyl;
$R^2$ is H or $CH_3$;
$R^{3A}$ is H, $CH_3$, $CH_2CH_3$, $CH(CH_3)_2$, $CH_2CH_2CH_3$, $CH_2CH(CH_3)_2$, $C(CH_3)_3$, $CH_2CH_2CH(CH_3)_2$, or $CH_2CH_2CH_2CH(CH_3)_2$
$R^{3B}$ is H or $CH_3$;
$R^4$ is:

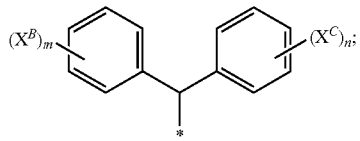

each $X^B$ and each $X^C$ are independently selected from the group consisting of: (1) $CH_3$, (2) $CH_2CH_3$, (3) $CF_3$, (4) OH, (5) $OCH_3$, (6) $OCF_3$, (7) Cl, (8) Br, (9) F, (10) CN, (11) $NH_2$, (12) $N(H)CH_3$, (13) $N(CH_3)_2$, (14) $C(O)CH_3$, (15) $C(O)OCH_3$, (16) $CH_2OH$, and (17) $CH_2OCH_3$;
m is an integer equal to 0, 1, or 2;
n is an integer equal to 0, 1, or 2;
each $X^A$ is independently: (1) $CH_3$, (2) $CH_2CH_3$, (3) $CF_3$, (4) OH, (5) $OCH_3$, (6) $OCF_3$, (7) Cl, (8) Br, (9) F, (10) CN, (11) $NH_2$, (12) $N(H)CH_3$, (13) $N(CH_3)_2$, (14) $C(O)CH_3$, (15) $C(O)OCH_3$, (16) $CH_2OH$, (17) $CH_2OCH_3$, (18) $CH_2NH_2$, (19) $CH_2N(H)CH_3$, (20) $CH_2N(CH_3)_2$, (21) $CH(CH_3)OH$, (22) $CH(CH_3)OCH_3$, (23) $CH(CH_3)NH_2$, (24) $CH(CH_3)N(H)CH_3$, or (25) $CH(CH_3)N(CH_3)_2$;
k is an integer equal to 0, 1, or 2;
or, alternatively, when two $X^A$ substituents are present on the phenyl ring and the two $X^A$ are attached to adjacent carbon atoms of the phenyl ring, the two $X^A$ are optionally taken together with the carbon atoms to which they are attached to form a 5- or 6-membered, saturated or unsaturated heterocycle fused to the phenyl ring, wherein the heterocycle contains from 1 to 2 heteroatoms independently selected from N, O and S; and
$R^5$ is $C(O)OCH_3$ or $C(O)OC(CH_3)_3$.

A first sub-class of the third class (Sub-class C3-S1) includes compounds of Formula I and pharmaceutically acceptable salts thereof, wherein $R^1$ is $CH(CH_3)_2$, $CH_2CH_2CH_3$, $CH_2CH(CH_3)_2$, $CH_2CH_2CH(CH_3)_2$, or $CH_2CH_2CH_2CH(CH_3)_2$; and all of the other variables are as defined in Class C3.

A second sub-class of the third class (Sub-class C3-S2) includes compounds of Formula I and pharmaceutically acceptable salts thereof, wherein the compounds are of Formula III; and all of the variables are as defined in Class C3. A subset of the sub-class includes compounds of Formula III and pharmaceutically acceptable salts thereof, wherein $R^1$ is $CH(CH_3)_2$, $CH_2CH_2CH_3$, $CH_2CH(CH_3)_2$, $CH_2CH_2CH(CH_3)_2$, or $CH_2CH_2CH_2CH(CH_3)_2$; and all of the other variables are as defined in Sub-class C3-S1.

A fourth class of compounds of the present invention (Class C4) includes compounds of Formula I and pharmaceutically acceptable salts thereof, wherein:
A is N—$R^1$;
B is N—$R^2$;
$R^1$ is $CH(CH_3)_2$, $CH_2CH(CH_3)_2$, $CH_2CH_2CH(CH_3)_2$, or $CH_2CH_2CH_2CH(CH_3)_2$;
$R^2$ is H or $CH_3$;
either (i) $R^{3A}$ is H, $CH_3$, $CH_2CH_3$, $CH(CH_3)_2$, $CH_2CH_2CH_3$, $CH_2CH(CH_3)_2$, $C(CH_3)_3$, $CH_2CH_2CH(CH_3)_2$, or $CH_2CH_2CH_2CH(CH_3)_2$, and $R^{3B}$ is H; or (ii) $R^{3A}$ and $R^{3B}$ are both $CH_3$;
$R^4$ is:

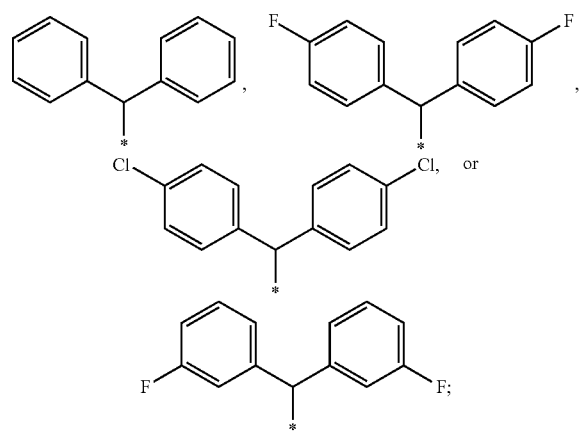

there are 1 or 2 $X^A$ groups on the phenylsulfonyl moiety wherein one $X^A$ is in the para position on the phenyl ring and is $CH_3$, Cl, Br, F, $NH_2$, $CH_2NH_2$, $C(O)CH_3$, $CH_2OH$, or $CH(CH_3)OH$; and the other, optional $X^A$ is in the meta position on the phenyl ring and is Cl, Br, or F;
or, alternatively, when two $X^A$ substituents are present on the phenyl ring and the two $X^A$ are attached to adjacent carbon atoms, the two $X^A$ are optionally taken together with the carbon atoms to which they are attached to form —$OCH_2O$— or —$OCH_2CH_2O$—; and
$R^5$ is $C(O)OCH_3$.

A first sub-class of the fourth class (Sub-class C4-S1) includes compounds of Formula I and pharmaceutically acceptable salts thereof, wherein $R^4$ is

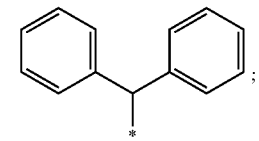 [SMILES: *C(c1ccccc1)c1ccccc1]

and all of the other variables are as defined in Class C4.

A second sub-class of the fourth class (Sub-class C4-S2) includes compounds of Formula I and pharmaceutically acceptable salts thereof, wherein $X^A$ is $NH_2$ in the para position on the phenyl; and all of the other variables are as defined in Class C4.

A third sub-class of the fourth class (Sub-class C4-S3) includes compounds of Formula I and pharmaceutically acceptable salts thereof, wherein $R^4$ is

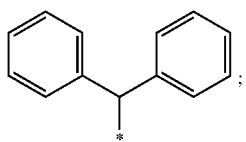

$X^4$ is NH$_2$ in the para position on the phenyl; and all of the other variables are as defined in Class C4.

A fourth sub-class of the fourth class (Sub-class C4-S4) includes compounds of Formula I and pharmaceutically acceptable salts thereof, wherein the compounds are of Formula III; and all of the variables are as defined in Class C4. A subset of the sub-class includes compounds of Formula III and pharmaceutically acceptable salts thereof, wherein R$^4$ is

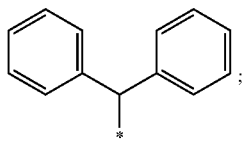 [SMILES: *C(c1ccccc1)c1ccccc1]

and all of the other variables are as defined in Sub-class C4-S4. Another subset of the sub-class includes compounds of Formula III and pharmaceutically acceptable salts thereof, wherein X$^4$ is NH$_2$ in the para position on the phenyl; and all of the other variables are as defined in Sub-class C4-S4. Another subset of the sub-class includes compounds of Formula III and pharmaceutically acceptable salts thereof, wherein R$^4$ is

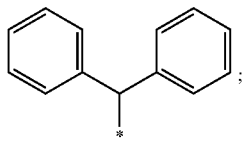 [SMILES: *C(c1ccccc1)c1ccccc1]

$X^4$ is NH$_2$ in the para position on the phenyl; and all of the other variables are as defined in Sub-class C4-S4.

Another embodiment of the present invention is a compound of Formula I, or a pharmaceutically acceptable salt thereof, wherein the compound is selected from the group consisting of the title compounds set forth in Examples 1 to 12 and pharmaceutically acceptable salts thereof.

Another embodiment of the present invention is a compound of Formula I, or a pharmaceutically acceptable salt thereof, as originally defined or as defined in any of the foregoing embodiments, sub-embodiments, aspects, classes, sub-classes or subsets, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis. The compounds of the invention have two or more asymmetric centers and can occur as mixtures of stereoisomers. It is understood that a substantially pure compound can be either a substantially pure mixture of stereoisomers or a substantially pure individual diastereomer or enantiomer.

Other embodiments of the present invention include the following:

(a) A pharmaceutical composition comprising an effective amount of a compound of Formula I as defined above, or a pharmaceutically acceptable salt thereof, and a pharmaceutically acceptable carrier.

(b) A pharmaceutical composition which comprises the product prepared by combining (e.g., mixing) an effective amount of a compound of Formula I as defined above, or a pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(e) The pharmaceutical composition of (d), wherein the antiviral is selected from the group consisting of HIV reverse transcriptase inhibitors and HIV integrase inhibitors.

(f) A combination which is (i) a compound of Formula I as defined above, or a pharmaceutically acceptable salt thereof, and (ii) an anti-HIV agent selected from the group consisting of HIV antiviral agents, immunomodulators, and anti-infective agents; wherein Compound I and the anti-HIV agent are each employed in an amount that renders the combination effective for inhibition of HIV protease, for treatment or prophylaxis of infection by HIV, or for treatment, prophylaxis of, or delay in the onset or progression of AIDS.

(g) The combination of (f), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(h) The combination of (g), wherein the antiviral is selected from the group consisting of HIV reverse transcriptase inhibitors and HIV integrase inhibitors.

(i) A method for the inhibition of HIV protease in a subject in need thereof which comprises administering to the subject an effective amount of a compound of Formula I or a pharmaceutically acceptable salt thereof.

(j) A method for the prophylaxis or treatment of infection by HIV (e.g., HIV-1) in a subject in need thereof which comprises administering to the subject an effective amount of a compound of Formula I or a pharmaceutically acceptable salt thereof.

(k) The method of (j), wherein the compound of Formula I is administered in combination with an effective amount of at least one other HIV antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(l) The method of (k), wherein the at least one other HIV antiviral is selected from the group consisting of HIV reverse transcriptase inhibitors and HIV integrase inhibitors.

(m) A method for the prophylaxis, treatment or delay in the onset or progression of AIDS in a subject in need thereof which comprises administering to the subject an effective amount of a compound of Formula I or a pharmaceutically acceptable salt thereof.

(n) The method of (m), wherein the compound is administered in combination with an effective amount of at least one other HIV antiviral, selected from the group consisting of HIV protease inhibitors, HIV reverse transcriptase inhibitors, HIV integrase inhibitors, HIV fusion inhibitors, HIV entry inhibitors, and HIV maturation inhibitors.

(o) The method of (n), wherein the at least one other HIV antiviral is selected from the group consisting of HIV reverse transcriptase inhibitors and HIV integrase inhibitors.

(p) A method for the inhibition of HIV protease in a subject in need thereof which comprises administering to the subject the pharmaceutical composition of (a), (b), (c), (d), or (e) or the combination of (e), (f), or (g).

(q) A method for the prophylaxis or treatment of infection by HIV (e.g., HIV-1) in a subject in need thereof which comprises administering to the subject the pharmaceutical composition of (a), (b), (c), (d), or (e) or the combination of (e), (f), or (g).

(r) A method for the prophylaxis, treatment, or delay in the onset or progression of AIDS in a subject in need thereof which comprises administering to the subject the pharmaceutical composition of (a), (b), (c), (d), or (e) or the combination of (e), (f), or (g).

The present invention also includes a compound of Formula I, or a pharmaceutically acceptable salt thereof, (i) for use in, (ii) for use as a medicament for, or (iii) for use in the manufacture/preparation of a medicament for: (a) therapy (e.g., of the human body), (b) medicine, (c) inhibition of HIV protease, (d) treatment or prophylaxis of infection by HIV, or (e) treatment, prophylaxis of, or delay in the onset or progression of AIDS. In these uses, the compounds of the present invention can optionally be employed in combination with one or more other anti-HIV agents selected from HIV antiviral agents, anti-infective agents, and immunomodulators.

Additional embodiments of the invention include the pharmaceutical compositions, combinations and methods set forth in (a)-(r) above and the uses (i)(a)-(e) through (iii)(a)-(e) set forth in the preceding paragraph, wherein the compound of the present invention employed therein is a compound of one of the embodiments, sub-embodiments, aspects, classes, sub-classes, subsets or features described above. In all of these embodiments etc., the compound can optionally be used in the form of a pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or a pharmaceutically acceptable carrier and optionally one or more excipients, it is understood that the term "substantially pure" is in reference to a compound of Formula I or its salt per se.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and isopropyl, ethyl and methyl. As another example, "$C_{1-3}$ alkyl" refers to n-propyl, isopropyl, ethyl and methyl.

The term "branched alkyl" refers to an alkyl group as defined above except that straight chain alkyl groups in the specified range are excluded. As defined herein, branched alkyl includes alkyl groups in which the alkyl is attached to the rest of the compound via a secondary or tertiary carbon; e.g., isopropyl is a branched alkyl group.

The term "cycloalkyl" refers to any monocyclic ring of an alkane having a number of carbon atoms in the specified range. Thus, for example, "$C_{3-6}$ cycloalkyl" (or "$C_3$-$C_6$ cycloalkyl") refers to cyclopropyl, cyclobutyl, cyclopentyl, and cyclohexyl, and "$C_{3-5}$ cycloalkyl" refers to cyclopropyl, cyclobutyl, and cyclopentyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.). A fluoroalkyl of particular interest is $CF_3$.

The term "C(O)" refers to carbonyl. The terms "$S(O)_2$" and "$SO_2$" each refer to sulfonyl. The term "S(O)" refers to sulfinyl.

An asterisk ("*") as the end of an open bond in a chemical group denotes the point of attachment of the group to the rest of the compound.

The term "aryl" refers to phenyl and naphthyl. The aryl of particular interest is phenyl.

The term "heteroaryl" refers to (i) a 5- or 6-membered heteroaromatic ring containing from 1 to 4 heteroatoms independently selected from N, O and S, or (ii) is a heterobicyclic ring selected from quinolinyl, isoquinolinyl, and quinoxalinyl. Suitable 5- and 6-membered heteroaromatic rings include, for example, pyridyl (also referred to as pyridinyl), pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. A class of heteroaryls of interest consists of (i) 5- and 6-membered heteroaromatic rings containing from 1 to 3 heteroatoms independently selected from N, O and S, and (ii) heterobicyclic rings selected from quinolinyl, isoquinolinyl, and quinoxalinyl. Heteroaryls of particular interest are pyrrolyl, imidazolyl, pyridyl, pyrazinyl, quinolinyl (or quinolyl), isoquinolinyl (or isoquinolyl), and quinoxalinyl.

Examples of 4- to 7-membered, saturated heterocyclic rings within the scope of this invention include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this invention (see HetB) include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings listed above are not a limitation on the rings which can be used in the present invention. These rings are merely representative.

Unless expressly stated to the contrary in a particular context, any of the various cyclic rings and ring systems described herein may be attached to the rest of the compound at any ring atom (i.e. any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, an aryl or heteroaryl described as optionally substituted with "from 1 to 4 substituents" is intended to include as aspects thereof, an aryl or heteroaryl substituted with 1 to 4 substituents, 2 to 4 substituents, 3 to 4 substituents, 4 substituents, 1 to 3 substituents, 2 to 3 substituents, 3 substituents, 1 to 2 substituents, 2 substituents, and 1 substituent.

When any variable (e.g., $X^A$ or $X^B$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., cycloalkyl, aryl, or heteroaryl) provided such ring substitution is chemically allowed and results in a stable compound.

The compounds of the invention contain chiral centers and, as a result of the selection of substituents and substituent patterns, can contain additional chiral centers, and thus can occur as mixtures of stereoisomers, or as individual diastereomers, or enantiomers. All isomeric forms of these compounds, whether individually or in mixtures, are within the scope of the present invention.

To the extent substituents and substituent patterns provide for the existence of tautomers (e.g., keto-enol tautomers) in the compounds of the invention, all tautomeric forms of these compounds, whether present individually or in mixtures, are within the scope of the present invention. Compounds of the present invention having a hydroxy substituent on a carbon atom of a heteroaromatic ring are understood to include compounds in which only the hydroxy is present, compounds in which only the tautomeric keto form (i.e., an oxo substitutent) is present, and compounds in which the keto and enol forms are both present.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I.

The methods of the present invention involve the use of compounds of the present invention in the inhibition of HIV protease (e.g., wild type HIV-1 and/or mutant strains thereof), the prophylaxis or treatment of infection by human immunodeficiency virus and the prophylaxis, treatment or delay in the onset or progression of consequent pathological conditions such as AIDS. Prophylaxis of AIDS, treating AIDS, delaying the onset or progression of AIDS, or treating or prophylaxis of infection by HIV is defined as including, but not limited to, treatment of a wide range of states of HIV infection: AIDS, ARC (AIDS related complex), both symptomatic and asymptotic, and actual or potential exposure to HIV. For example, the present invention can be employed to treat infection by HIV after suspected past exposure to HIV by such means as blood transfusion, exchange of body fluids, bites, accidental needle stick, or exposure to patient blood during surgery.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, or benzoic acid. When compounds employed in the present invention carry an acidic moiety (e.g., —COOH or a phenolic group), suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts.

The term "administration" and variants thereof (e.g., "administering" a compound) in reference to a compound of Formula I mean providing the compound to the individual in need of treatment or prophylaxis. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV protease (wild type and/or mutant strains thereof) and thereby elicit the response being sought (i.e., an "inhibition effective amount"). When the active compound (i.e., active ingredient) is administered as the salt, references to the amount of active ingredient are to the free form (i.e., the non-salt form) of the compound.

In the methods of the present invention (i.e., inhibiting HIV protease, treating or prophylaxis of HIV infection or treating, prophylaxis of, or delaying the onset or progression of AIDS), the compounds of Formula I, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18$^{th}$ edition, edited by A. R. Gennaro, Mack Publishing Co., 1990 and in *Remington—The Science and Practice of Pharmacy*, 21st edition, Lippincott Williams & Wilkins, 2005.

The compounds of Formula I can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of a compound of Formula I with one or more anti-HIV agents. An "anti-HIV agent" is any agent which is directly or indirectly effective in the inhibition of HIV reverse transcriptase, protease, or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds of the present invention include, for example, those listed in Table A as follows:

TABLE A

Antiviral Agents for Treating HIV infection or AIDS

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| efavirenz, EFV, Sustiva ®, Stocrin ® | nnRTI |
| efavirenz + emtricitabine + tenofovir DF, Atripla ® | nnRTI + nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

It is understood that the scope of combinations of the compounds of this invention with anti-HIV agents is not limited to the HIV antivirals listed in Table A and/or listed in the above-referenced Tables in WO 01/38332 and WO 02/30930, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57th edition (2003), the 58th edition (2004), or the 59th edition (2005). The dosage ranges for a compound of the invention in these combinations are the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

Abbreviations employed herein include the following: APCI=atmospheric pressure chemical ionization (mass spectroscopy); Bn=benzyl; Boc=t-butyloxycarbonyl; Boc-ON=2-(tert-butoxycarbonyloxyamino)-2-phenyl acetonitrile; $Boc_2O$=di-t-butyl carbonate; BSA=bovine serum albumin; Cbz=benzyloxycarbonyl; DBU=1,8-diazabicyclo[5.4.0]undec-7-one; DIPEA=diisopropylethylamine (or Hunig's base); DMF=dimethylformamide; DMSO=dimethyl sulfoxide; DPPA=diphenylphosphoryl azide; Et=ethyl; EtOAc=ethyl acetate; EtOH=ethanol; FBS=fetal bovine serum; Fmoc=9-fluorenylmethoxycarbonyl; HPLC=high performance liquid chromatography; HSu=hydroxy succinimide; LC-MS=liquid chromatography-mass spectroscopy; m-CPBA=meta-chloroperbenzoic acid; Me=methyl; MeOH=methanol; Moc=methoxycarbonyl; Ms=mesyl or methanesulfonyl; i-Am=isoamyl; i-Bu=isobutyl; n-Bu=n-butyl; NMR=nuclear magnetic resonance; n-Pr=n-propyl; Ph=phenyl; RP-HPLC=reverse phase HPLC; STAB=sodium triacetoxyborohydride; TEA=triethylamine; TFA=trifluoroacetic acid; THF=tetrahydrofuran.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The term "Ar" appears in several of the schemes and refers to phenyl optionally substituted with one or more $X^A$.

Scheme 1 below depicts a method for preparing trans 3,4-diaminopyrrolidine compounds of the present invention, wherein L-tartaric acid 1-1 is treated with benzylamine to afford (3R,4R)-1-benzyl-3,4-dihydroxypyrrolidine-2,5-dione 1-2 which can then be treated with an appropriate reducing agent such as $LiAlH_4$ to obtain (3S,4S)-1-benzylpyrrolidine-3,4-diol 1-3. Diol 1-3 can then be converted to (3R,4R)-3,4-diazido-1-benzylpyrrolidine 1-4 by mesylation and treatment with sodium azide. Diazide 1-4 can then be treated with triphenylphosphine as described in *J. Am. Chem. Soc.* 1998, vol. 120, p. 9112 to give (3R,4R)-4-azido-1-benzylpyrrolidin-3-amine 1-5, which can then be protected with a suitable protecting group such as Boc using di-t-butylcarbonate or Boc-ON or the like to afford 1-6. Further azide reduction using a reagent such as triphenylphosphine can afford the mono protected diamine 1-7, which can then be sulfonylated using an arylsulfonyl chloride and an acid scavenger to afford arylsulfonylated amine 1-8, which can then be N-alkylated using an appropriately substituted alkyl halide, or alkyl alcohol under Mitsunobu conditions. Alkylated amine 1-9 can then be deprotected (e.g., cleavage of Boc by treatment with acid) and the resulting amine 1-10 can then be reductively aminated using an appropriately substituted N-protect-edamino aldehyde to give product 1-11, which can in turn be deprotected (e.g., Boc removal by treatment with acid) to afford amine 1-12. Amine 1-12 can then be coupled with a suitably protected amino acid derivative to give coupled product (amide) 1-13. The secondary amine can then be functionalized to add $R^2$ (e.g., alkylated), the benzyl group protecting the pyrrolidinyl nitrogen can be removed (e.g., by treatment with 1-chloroethyl chloroformate), and the aryl sulfonamide can optionally be further functionalized (i.e., adding and/or changing substituents on the phenyl ring to give Ar', such as reducing Ar=p-nitrophenyl to Ar'=p-aminophenyl by treatment with $SnCl_2$) to give the final targets 1-14.

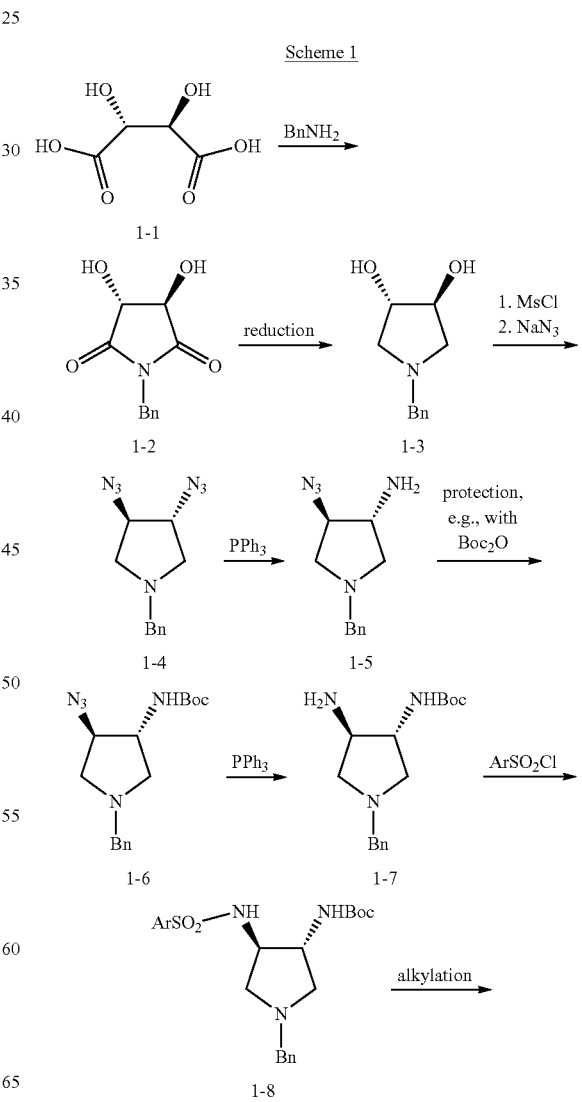

Scheme 1

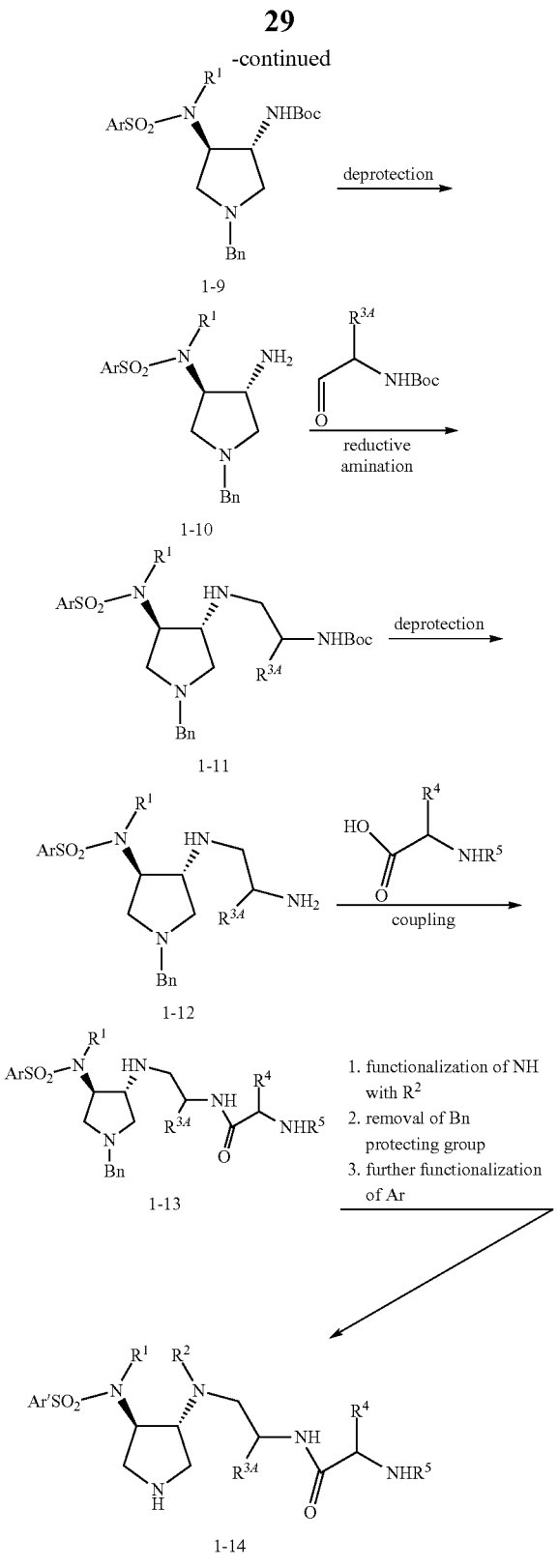

1996, p. 747 (see Scheme 14). The O- and N-benzyl groups can then be removed and a carbamate, (e.g., Boc) formed at the pyrrolidinyl N by hydrogenation in the presence of a carbamate-forming reagent (e.g., Boc$_2$O). The resulting acid 2-4 can then be reacted under conditions known to effect a Curtius rearrangement (e.g., treatment with BnOH and DPPA) to afford 2-5. The ester functional group in 2-5 can then be converted to the aldehyde 2-6 in a two-step procedure by, for example, treating with a reducing agent (e.g., LiBH$_4$) then oxidizing the formed alcohol with a reagent such as manganese(IV)oxide and the aldehyde can then be olefinated (e.g., by coupling with methyl (triphenylphosphoranilydene) acetate) to give the unsaturated ester 2-7. The ester 2-7 can then be reduced (e.g., by treatment with LiAlH$_4$) to the saturated alcohol 2-8. The Cbz protecting group can then be removed via hydrogenolysis and the resulting amine 2-9 sulfonylated with an arylsulfonyl chloride such as p-nitrobenzenesulfonyl chloride to provide 2-10. Arylsulfonamide 2-10 can then be alkylated (e.g., with an alkyl halide and base) to introduce R$^1$ and thereby afford intermediate compound 2-11. The hydroxy group in 2-11 can be converted to azide using standard methodology (e.g., by treatment with mesyl chloride and then with NaN$_3$) to obtain 2-12, which can be reduced (e.g., by treatment with PPh$_3$) to amine 2-13. Amine 2-13 can then be coupled with a suitably protected amino acid derivative to give coupled product (amide) 2-14. The Boc group protecting the pyrrolidinyl nitrogen can be removed (e.g., by treatment with acid), and the aryl sulfonamide can optionally be further functionalized (i.e., adding and/or changing substituents on the phenyl ring to give Ar', such as reducing Ar=p-nitrophenyl to Ar'=p-aminophenyl by treatment with SnCl$_2$) to give the final targets 2-15.

Scheme 2

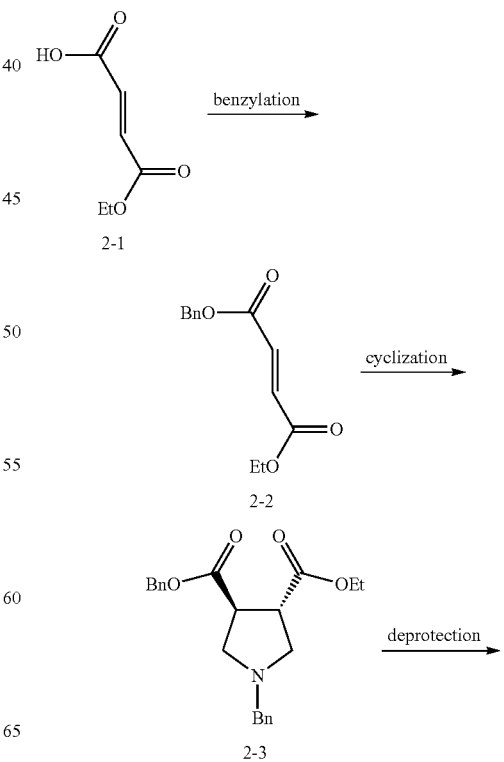

Scheme 2 depicts a method for preparing trans 3-amino-4-alkyl pyrrolidine compounds of the invention, wherein monoethyl fumarate 2-1 can be benzylated (e.g., by treatment with BnBr in the presence of DBU) to compound 2-2, and then cyclized into pyrrolidine derivative 2-3 (e.g., by treatment of 2-2 with PhCH$_2$NHCH$_2$SiMe$_3$ as described in *Chem. Lett.*

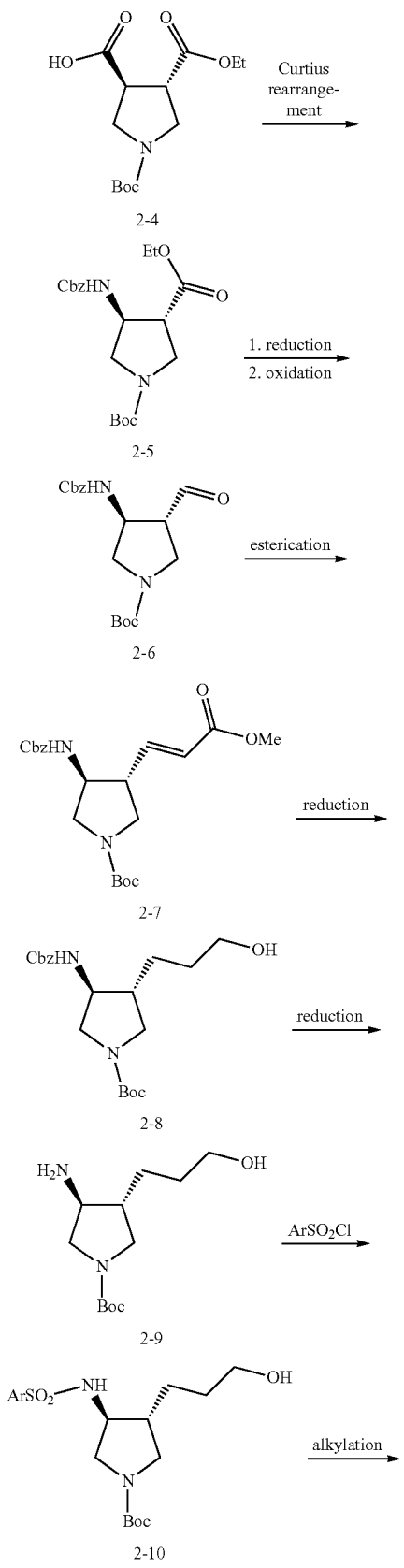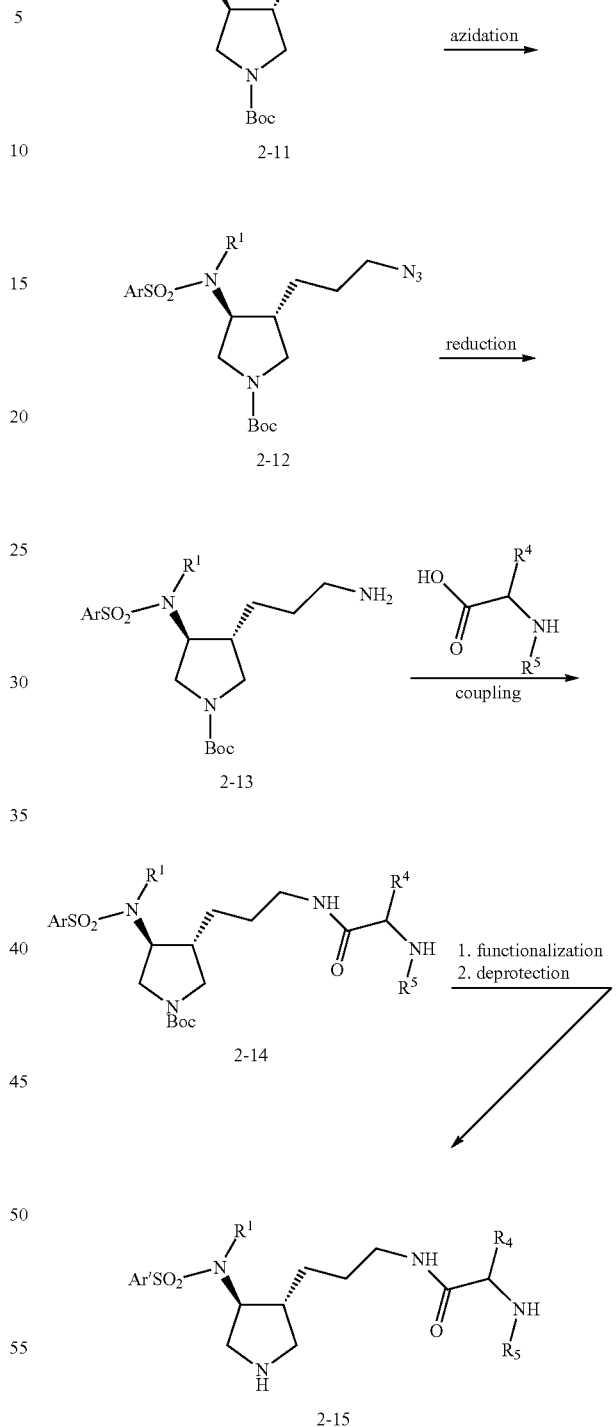
The following examples serve only to illustrate the invention and its practice. The examples are not to be construed as limitations on the scope or spirit of the invention.
The term "room temperature" in the examples refers to the ambient temperature which was typically in the range of about 19° C. to 26° C.

Example 1

N-(2-{[(3R,4R)-4-{[(4-aminophenyl)sulfonyl](3-methylbutyl)amino}pyrrolidin-3-yl]amino}ethyl)-Nα-(methoxycarbonyl)-β-phenyl-L-phenylalaninamide

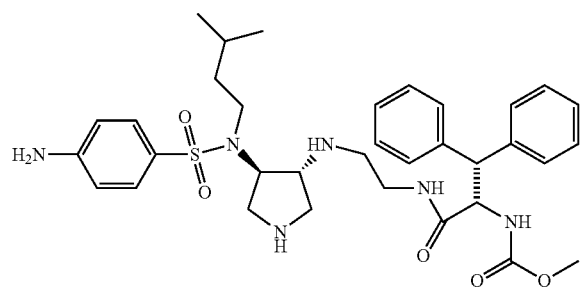 [SMILES: COC(=O)N[C@H](C(=O)NCCN[C@@H]1CNC[C@H]1N(CCC(C)C)S(=O)(=O)c1ccc(N)cc1)C(c1ccccc1)c1ccccc1]

Step 1 (3R,4R)-1-Benzyl-3,4-dihydroxypyrrolidine-2,5-dione

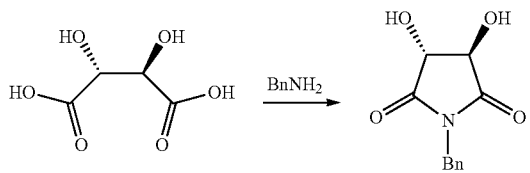

L-Tartaric acid (90 g, 600 mmol) and benzylamine (64.3 g, 600 mmol) were mixed in 400 mL of o-xylene and the mixture was refluxed 14 hours with a Dean-Stark trap. The pellet was filtered off and the compound was crystallized from hot EtOH (1600 mL). The formed crystals were washed with cold hexane to afford the title compound.

Step 2 (3S,4S)-1-Benzylpyrrolidine-3,4-diol

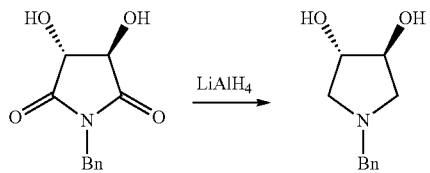

To a suspension of LiAlH$_4$ (18.33 g, 219.2 mmol) in 200 mL THF, (3R,4R)-1-benzyl-3,4-dihydroxypyrrolidine-2,5-dione (23.1 g, 104.4 mmol) was added and the mixture was refluxed for 12 hours. The mixture was cooled down to room temperature and carefully quenched with 3 mL EtOAc and 3 mL MeOH. Wet silica gel was added to the mixture following by addition of MeOH—CHCl$_3$, 1:1, and the mixture was filtered. The filtrate was evaporated giving the title compound that was used for the next step without additional purification.

Step 3 (3R,4R)-3,4-Diazido-1-benzylpyrrolidine

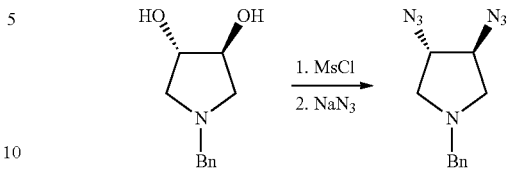

To a mixture of (3S,4S)-1-benzylpyrrolidine-3,4-diol (14.8 g, 76.6 mmol) and Et$_3$N (23.3 g, 229.8 mmol) in 300 mL CH$_2$Cl$_2$, MsCl (26.3 g, 229.8 mmol) was added dropwise at 0° C. The mixture was stirred at room temperature for 1 hour, water was added following by addition of 1N HCl. The aqueous acidic layer was washed with CH$_2$Cl$_2$ and basified with 50% aqueous NaOH. The mixture was extracted with CH$_2$Cl$_2$, the combined organic extracts were dried with Na$_2$SO$_4$ and evaporated. The residue was dissolved in 300 mL DMSO, and sodium azide (16.9 g, 260 mmol) was added. The mixture was stirred at 90° C. for 24 hours, cooled down to room temperature, diluted with 1200 mL of water, and extracted with Et$_2$O. The combined organic extracts were dried with Na$_2$SO$_4$ and evaporated. The residue was purified by column chromatography on silica gel eluting with 2→5% Et$_2$O in hexane giving the desired diazide.

Step 4 (3R,4R)-4-Azido-1-benzylpyrrolidin-3-amine

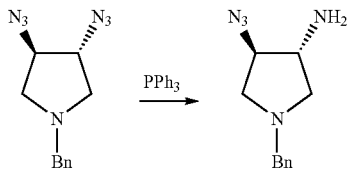 [SMILES: [N-]=[N+]=N[C@@H]1CN(Cc2ccccc2)C[C@H]1N=[N+]=[N-] ; [N-]=[N+]=N[C@@H]1CN(Cc2ccccc2)C[C@H]1N ; "PPh3"]

To a solution of diazide prepared as described in Step 3 (8.9 g, 36.5 mmol) in 350 mL PhMe, PPh$_3$ 9.6 g, 36.5 mmol) was added and the mixture was refluxed for 1 hour. The mixture was cooled down to room temperature, diluted with 350 mL THF, water (1.31 g, 73.0 mmol) was added and the mixture was refluxed for additional 1 hour. 4N HCl was added, the aqueous acidic layer was separated, washed with CHCl$_3$ and basified with aqueous NH$_3$ to pH 9-10. The product was extracted with CHCl$_3$, the combined organic extracts were dried with Na$_2$SO$_4$ and evaporated giving the title compound.

Step 5 tert-Butyl (3R,4R)-4-azido-1-benzylpyrrolidin-3-ylcarbamate

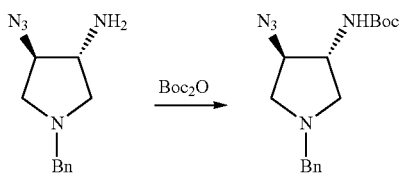 [SMILES: "Boc2O" ; [N-]=[N+]=N[C@@H]1CN(Cc2ccccc2)C[C@H]1N ; CC(C)(C)OC(=O)N[C@@H]1CN(Cc2ccccc2)C[C@H]1N=[N+]=[N-]]

To a solution of (3R,4R)-4-azido-1-benzylpyrrolidin-3-amine (6.5 g, 22.3 mmol) in 100 mL THF, Boc$_{20}$ (4.9 g, 22.3 mmol) was added and the mixture was stirred at reflux for 0.5 hour. The mixture was taken to dryness giving the desired compound (7.15 g). $^1$H NMR (400 MHz, DMSO-$d_6$): 1.38 (9H, s), 2.21 (1H, dd, $J_1$=7.1 Hz, $J_2$=9.3 Hz), 2.58 (1H, dd, $J_1$=3.4 Hz, $J_2$=10.0 Hz), 2.67 (1H, dd, $J_1$=6.8 Hz, $J_2$=10.3 Hz), 2.96 (1H, dd, $J_1$=1.5 Hz, $J_2$=8.3 Hz), 3.50 (1H, d, J=13.2 Hz), 3.60 (1H, d, J=13.2 Hz), 3.75-3.87 (2×m, 2×1H), 7.22-7.33 (5H, m). LC-MS APCI: m/z 318.1 [M+H]$^+$.

Step 6 tert-Butyl (3R,4R)-4-amino-1-benzylpyrrolidin-3-ylcarbamate

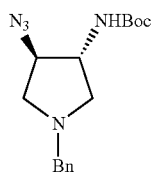 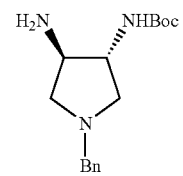

To a solution of tert-butyl (3R,4R)-4-azido-1-benzylpyrrolidin-3-ylcarbamate (7.0 g, 22.0 mmol) in 250 mL toluene, PPh$_3$ 6.0 g, 23.0 mmol) was added and the mixture was refluxed for 1 hour. The mixture was cooled down to room temperature, diluted with 250 mL THF, water (0.54 g, 30.0 mmol) was added and the mixture was refluxed for an additional 1 hour. 4N HCl was added, the aqueous acidic layer was separated, washed with CHCl$_3$ and basified with aqueous NH$_3$ to pH 9-10. The product was extracted with CHCl$_3$, the combined organic extracts were dried with Na$_2$SO$_4$ and evaporated. The residue was purified by column chromatography on silica gel eluting with 10% MeOH in CHCl$_3$ giving the title mono-Boc protected diamine.

Step 7 tert-Butyl [(3R,4R)-1-benzyl-4-{[(4-nitrophenyl)sulfonyl]amino}pyrrolidin-3-yl]carbamate

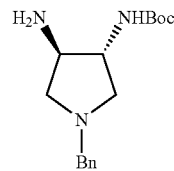

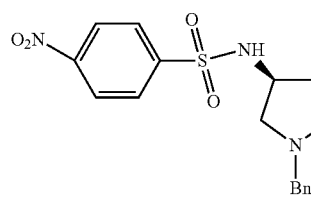

To a solution of tert-butyl (3R,4R)-4-amino-1-benzylpyrrolidin-3-ylcarbamate (5.8 g, 20 mmol) in 100 mL of CH$_2$Cl$_2$, triethylamine (4.04 g, 40 mmol) was added following by addition of 4-nitrobenzenesulfonyl chloride (1.1 eq) and the mixture was stirred at room temperature overnight. The reaction was quenched with saturated aqueous NH$_4$Cl, extracted with CH$_2$Cl$_2$, the combined organic extracts were dried with Na$_2$SO$_4$ and evaporated. The residue was purified by column chromatography on silica gel eluting with 1-2% MeOH in CHCl$_3$ to give the title product.

Step 8 tert-Butyl [(3R,4R)-1-benzyl-4-{(3-methylbutyl)[(4-nitrophenyl)sulfonyl]amino}pyrrolidin-3-yl]carbamate

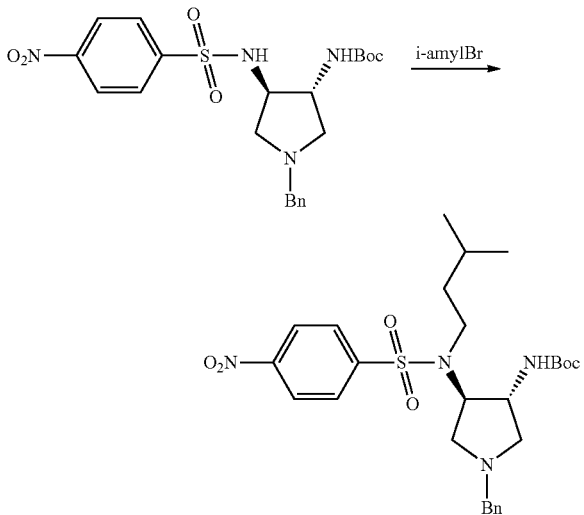

A mixture of tert-butyl [(3R,4R)-1-benzyl-4-{[(4-nitrophenyl)sulfonyl]amino}pyrrolidin-3-yl]carbamate (4.76 g, 10 mmol), isoamyl bromide (1.2 eq), and K$_2$CO$_3$ (2.76 g, 20 mmol) in 50 mL of DMF was stirred overnight at 50° C. The mixture was diluted with H$_2$O, extracted with EtOAc, the combined organic extracts were dried with Na$_2$SO$_4$ and evaporated. The residue was purified by column chromatography on silica gel eluting with 5→20% EtOAc in hexane to give the title product.

Step 9 N-[(3R,4R)-4-Amino-1-benzylpyrrolidin-3-yl]-N-methyl-4-nitrobenzenesulfonamide

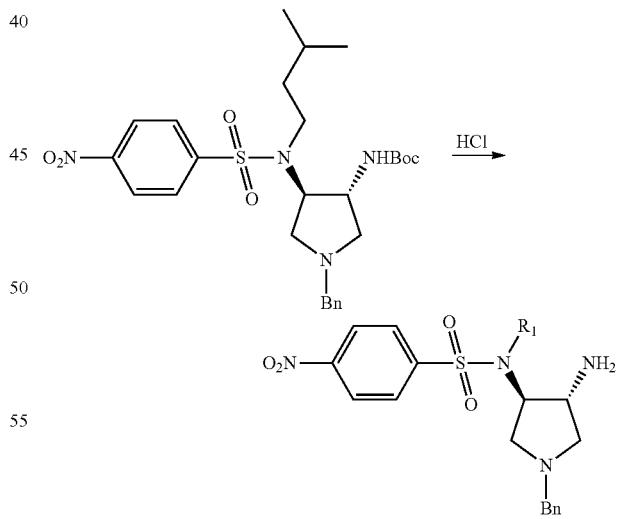

A solution of tert-butyl [(3R,4R)-1-benzyl-4-{(3-methylbutyl)[(4-nitrophenyl)sulfonyl]amino}pyrrolidin-3-yl]carbamate in 2N HCl dioxane was stirred overnight at room temperature. The solvent was evaporated to a minimal volume, diethyl ether was added, and the formed pellet was filtered off and washed with diethyl ether giving the crude title product which was used in the next step without purification.

Step 10 tert-Butyl (2-{[(3R,4R)-1-benzyl-4-{(3-methylbutyl)[(4-nitrophenyl)sulfonyl]amino}pyrrolidin-3-yl]amino}ethyl)carbamate

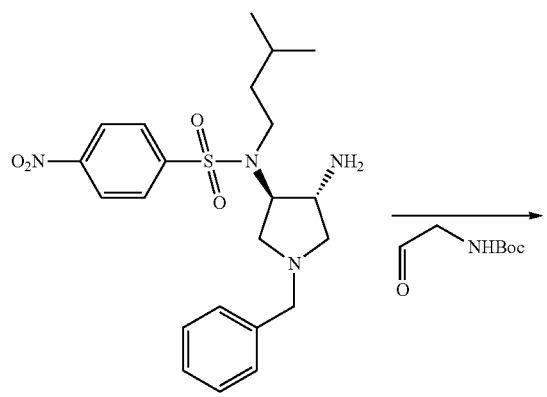

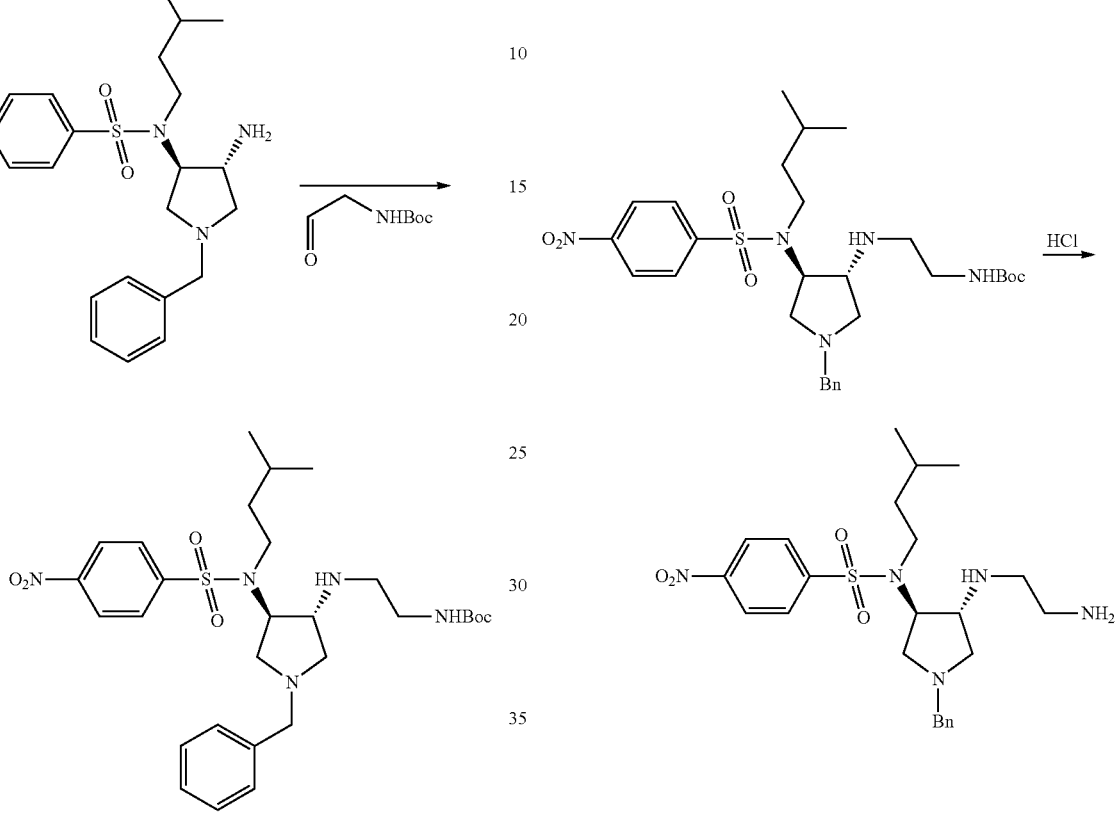

To a solution of N-[(3R,4R)-4-amino-1-benzylpyrrolidin-3-yl]-N-methyl-4-nitrobenzenesulfonamide (692 mg, 1.5 mmol) in MeOH was added K$_2$CO$_3$ (405 mg, 3 mmol) and the mixture was stirred for 0.5 hour at room temperature. To this mixture, Boc-amino glycinal (1.8 mmol) was added following by addition of a solution of NaBH$_3$CN (111 mg, 1.8 mmol) and ZnCl$_2$ (0.6 eq) in MeOH at room temperature. The reaction mixture was stirred at room temperature overnight, quenched with 1N aqueous NaOH, extracted with CHCl$_3$, the combined organic extracts were dried with Na$_2$SO$_4$ and evaporated. The residue was purified by column chromatography on silica gel eluting with 2-5% MeOH in CHCl$_3$ giving the desired product.

Step 11 N-{(3R,4R)-4-[(2-Aminoethyl)amino]-1-benzylpyrrolidin-3-yl}-N-(3-methylbutyl)-4-nitrobenzenesulfonamide A solution of tert-butyl (2-{[(3R,4R)-1-benzyl-4-{(3-methylbutyl)[(4-nitrophenyl)sulfonyl]amino}pyrrolidin-3-yl]amino}ethyl)carbamate in 2N HCl dioxane was stirred overnight at room temperature before the solvent was evaporated to dryness. The resulting tris HCl salt was used directly in the next reaction.

Step 12 N-(2-{[(3R,4R)-1-Benzyl-4-{(3-methylbutyl)[(4-nitrophenyl)sulfonyl]amino}pyrrolidin-3-yl]amino}ethyl)-Nα-(methoxycarbonyl)-β-phenyl-L-phenylalaninamide

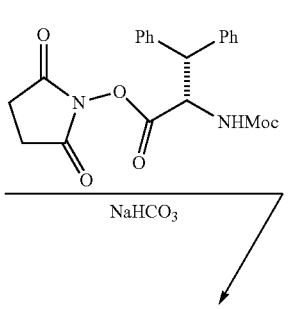

-continued

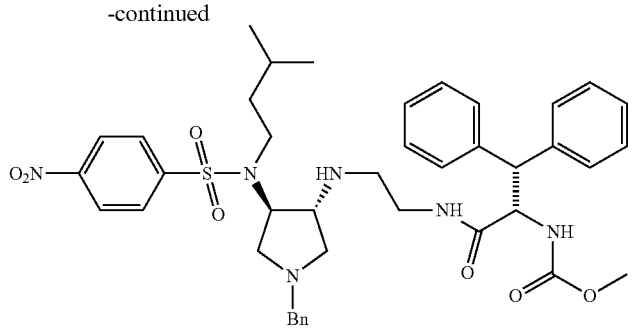

A mixture of an amine salt prepared as described in Step 11 (437 mg, 1 mmol), saturated aqueous NaHCO$_3$, and methoxycarbonyl-L-di-Phe-Hsu ester (322 mg, 1 mmol) in acetone-THF, 1:1, was stirred 2 hours at room temperature. To the mixture H$_2$O was added, and the product was extracted with CHCl$_3$. The combined organic extracts were dried with Na$_2$SO$_4$ and evaporated giving the crude product that was used for the next step without additional purification. LC-MS APCI: m/z 771.3 [M+H]$^+$.

Step 13  Nα-(Methoxycarbonyl)-N-(2-{[(3R,4R)-4-{(3-methylbutyl)[(4-nitrophenyl)sulfonyl]amino}pyrrolidin-3-yl]amino}ethyl)-β-phenyl-L-phenylalaninamide

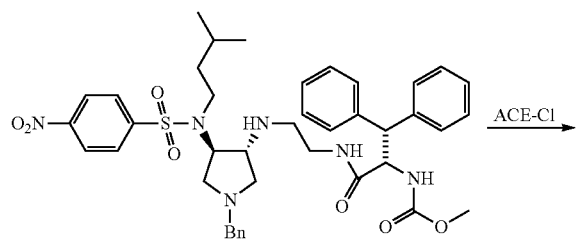

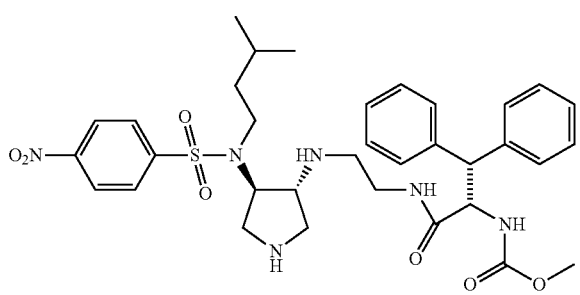

A mixture of the product prepared as described in Step 12 (1 eq), 1-chloroethyl chloroformate (3 eq) in 1,2-dichloroethane was stirred overnight at reflux. The solvent was evaporated, the residue was re-dissolved in MeOH and the mixture was refluxed for 1 hour. MeOH was evaporated and the residue containing compound the deprotected pyrrolidine was used for the next step without additional purification. LC-MS APCI: m/z 681.3 [M+H]$^+$.

Step 14 N-(2-{[(3R,4R)-4-{[(4-Aminophenyl)sulfonyl](3-methylbutyl)amino}pyrrolidin-3-yl]amino}ethyl)-Nα-(methoxycarbonyl)-β-phenyl-L-phenylalaninamide

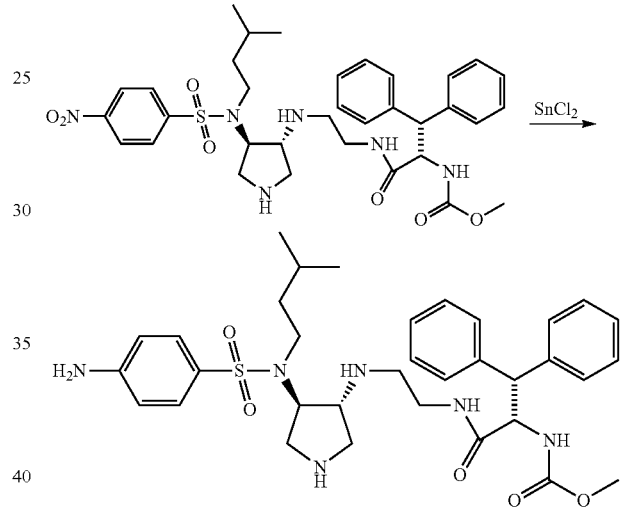

To a mixture of Nα-(methoxycarbonyl)-N-(2-{[(3R,4R)-4-{(3-methylbutyl)[(4-nitrophenyl)sulfonyl]amino}pyrrolidin-3-yl]amino}ethyl)-β-phenyl-L-phenylalaninamide (340 mg, 0.5 mmol), anhydrous SnCl$_2$ (564 mg, 2.5 mmol) in EtOAc, H$_2$O (10 eq) was added and the mixture was stirred at reflux for 2 hours. Saturated aqueous NaHCO$_3$ was added following by addition of water, the mixture was extracted with EtOAc, the combined organic extracts were dried with Na$_2$SO$_4$ and evaporated. The residue was purified by preparative RP-HPLC. The collected fractions were partially evaporated, basified with 1M K$_2$CO$_3$, and extracted with CH$_2$Cl$_2$. The combined organic extracts were dried with Na$_2$SO$_4$ and evaporated. The residue was re-dissolved in 0.5 mL CH$_2$Cl$_2$ and 1-2 mL of 2N HCl in Et$_2$O was added. The mixture was diluted with Et$_2$O, the pellet was filtered off, washed with Et$_2$O and dried in vacuo at 50-60° C. giving target compounds as tris-hydrochloride salts. $^1$H NMR (400 MHz, CD$_3$OD): 0.91 and 0.92 (6H, two d, J=6.5 Hz), 1.45-1.65 (3H, m), 2.90-3.01 (2H, br. m), 3.11-3.30 (4H, m), 3.34-3.41 (1H, m), 3.45-3.55 (2H, m), 3.57 (3H, s), 3.87 (1H, dd, J=13.0 Hz, J=8.0 Hz), 4.17-4.26 (1H, m), 4.355 (1H, d, J=11.0 Hz), 4.68-4.78 (1H, m), 4.92 (1H, d, J=11.0 Hz), 6.83-6.88 (2H, m), 7.18-7.24 (1H, m), 7.26-7.34 (7H, m), 7.34-7.39 (2H, m), 7.63-7.68 (2H, m). LC-MS APCI: m/z 651.3 [M+H]$^+$.

Examples 2-9

The compounds in the following table were prepared in a manner similar to Example 1 by substituting the appropriately substituted alkyl group in Step 8 or amino acid aldehyde in Step 10.

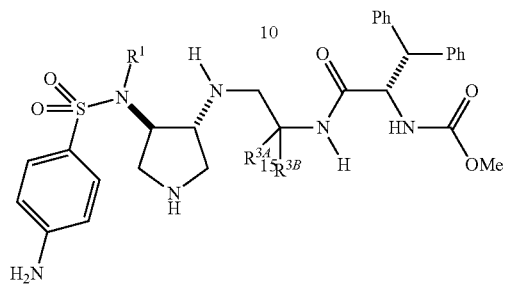

| Ex. No. | $R^1$ | $R^{3A}$, $R^{3B}$ | Name | $^1$H NMR |
|---|---|---|---|---|
| 2 | i-Am | Me, H | N-[(2S)-1-{[(3R,4R)-4-{[(4-aminophenyl)sulfonyl](3-methylbutyl)amino}pyrrolidin-3-yl]amino}propan-2-yl]-Nα-(methoxycarbonyl)-β-phenyl-L-phenylalaninamide | (400 MHz, CD$_3$OD): 0.91 and 0.915 (6H, two d, J = 6.5 Hz), 1.105 (3H, d, J = 7.0 Hz), 1.43-1.65 (3H, m), 2.48-2.58 (1H, br. m), 2.82-2.92 (1H, br. m), 3.15-3.28 (2H, m), 3.40-3.53 (2H, m), 3.57 (3H, s), 3.57-3.66 (1H, m), 3.77-3.89 (2H, m), 4.15-4.25 (1H, m), 4.35 (1H, d, J = 11.0 Hz), 4.65-4.74 (1H, m), 4.98 (1H, d, J = 11.0 Hz), 6.83-6.88 (2H, m), 7.18-7.41 (10H, m), 7.64-7.70 (2H, m). |
| 3 | i-Am | Et, H | N-[(2S)-1-{[(3R,4R)-4-{[(4-aminophenyl)sulfonyl](3-methylbutyl)amino}pyrrolidin-3-yl]amino}butan-2-yl]-Nα-(methoxycarbonyl)-β-phenyl-L-phenylalaninamide | (400 MHz, CD$_3$OD): 0.43 and 0.81 (3H, two t, J = 7.0 Hz), 0.90-0.96 and 1.00-1.14 (7H, two m), 1.40-1.67 (4H, m), 2.55-2.65 and 2.95-3.30 (3H, two m), 3.35-4.05 (6H, m), 3.57 and 3.60 (3H, two s), 4.10-4.43 (2H, m), 4.85-5.05 (2H, m), 7.05-7.13 (2H, m), 7.15-7.44 (10H, m), 7.75-7.85 (2H, m). |
| 4 | i-Am | n-Bu, H | N-(1-{[(3R,4R)-4-{[(4-aminophenyl)sulfonyl](3-methylbutyl)amino}pyrrolidin-3-yl]amino}hexan-2-yl)-Nα-(methoxycarbonyl)-β-phenyl-L-phenylalaninamide | (400 MHz, CD$_3$OD): 0.60-0.80 (1H, br. m), 0.83 and 0.92 (3H, two t, J = 7.0 Hz), 0.88-0.94 (6H, m), 0.94-1.20 (4H, m), 1.40-1.70 (4H, m), 2.62-2.72 and 2.98-3.28 (3H, two m), 3.35-3.70 (4H, m), 3.59 and 3.60 (3H, two s), 3.74-4.02 (2H, m), 4.20-4.42 (2H, m), 4.80-4.87 (1H, overlapping m), 4.91 and 5.00 (1H, d, J = 11.5 Hz), 6.81-6.87 (2H, m), 7.16-7.43 (10H, m), 7.60-7.69 (2H, m). |
| 5 | i-Am | i-Bu, H | N-[(2S)-1-{[(3R,4R)-4-{[(4-aminophenyl)sulfonyl](3-methylbutyl)amino}pyrrolidin-3-yl]amino}-4-methylpentan-2-yl]-Nα-(methoxycarbonyl)-β-phenyl-L-phenylalaninamide | (400 MHz, CD$_3$OD): 0.79 and 0.87 (6H, two d, J = 6.0 Hz), 0.90 (6H, d, J = 6.5 Hz), 1.18-1.65 (6H, m), 2.72-2.74 (1H, m), 2.98-3.27 (3H, m), 3.33-3.42 (1H, m), 3.47-3.66 (2H, m), 3.59 (3H, s), 3.81 (1H, dd, J = 13.0 Hz, J = 8.5 Hz), 3.87-3.97 (1H, m), 4.22-4.32 (1H, m), 4.38 (1H, d, J = 11.0 Hz), 4.80-4.87 (1H, m), 4.98 (1H, d, J = 11.0 Hz), 6.85-6.91 (2H, m), 7.18-7.26 (2H, m), 7.27-7.34 (4H, m), 7.34-7.43 (4H, m), 7.64-7.70 (2H, m). |
| 6 | i-Am | Me, Me | N-(1-{[(3R,4R)-4-{[(4-aminophenyl)sulfonyl](3-methylbutyl)amino}pyrrolidin-3-yl]amino}-2-methylpropan-2-yl)-Nα-(methoxycarbonyl)-β-phenyl-L-phenylalaninamide | (400 MHz, CD$_3$OD): 0.89-0.95 (6H, m), 0.915 (3H, s), 1.23 (3H, s), 1.42-1.64 (3H, m), 2.83 (1H, br. d, J = 13.0 Hz), 3.09 (1H, d, J = 13.0 Hz), 3.24-3.30 (1H, m), 3.45-3.53 (1H, m), 3.56 (3H, s), 3.55-3.65 (3H, m), 3.855 (1H, dd, J = 13.0 Hz, J = 8.5 Hz), 4.16 (1H, dt, J = 7.5 Hz, J = 7.5 Hz), 4.28 (1H, d, J = 11.5 Hz), 4.725 (1H, dt, J = 7.5 Hz, J = 7.5 Hz), 5.02 (1H, d, J = 11.5 Hz), 6.81-6.86 (2H, m), 7.18-7.27 (2H, m), 7.28-7.36 (4H, m), 7.36-7.42 (4H, m), 7.64-7.70 (2H, m). |
| 7 | i-Bu | H, H | N-(2-{[(3R,4R)-4-{[(4-aminophenyl)sulfonyl](2-methylpropyl)amino}pyrrolidin-3-yl]amino}ethyl)-Nα-(methoxycarbonyl)-β-phenyl-L-phenylalaninamide | (400 MHz, DMSO-d$_6$): 0.84 and 0.935 (6H, two d, J = 6.5 Hz), 1.92-2.08 (1H, m), 2.70-2.85 (2H, m), 2.86 (2H, d, J = 7.5 Hz), 2.98-3.35 (4H, m), 3.43 (3H, s), 3.55-3.80 (3H, overlapping m), 4.31 (1H, d, J = 11.5 Hz), 4.76-4.93 (2H, m), 6.68 (2H, d, J = 9.0 Hz), 7.12-7.20 (2H, m), 7.21-7.35 (8H, m), 7.47 (2H, d, J = 9.0 Hz), 8.32 (1H, br. t, J = 5.0 Hz), 9.51 (1H, br. s), 9.88 (1H, br. s), 10.00 (2H, br. s). |
| 8 | i-Pr | H, H | N-(2-{[(3R,4R)-4-{[(4-aminophenyl)sulfonyl](isopropyl)amino}pyrrolidin-3-yl]amino}ethyl)-Nα-(methoxycarbonyl)-β-phenyl-L-phenylalaninamide | (400 MHz, CD$_3$OD): 1.12 and 1.25 (6H, two d, J = 6.5 Hz), 2.64-2.74 (1H, m), 3.02-3.11 (1H, m), 3.22-3.28 (1H, m), 3.57 (3H, s), 3.56-3.62 (1H, m), 3.71-3.83 (3H, m), 3.96 (1H, dd, J = 12.5 Hz, J = 8.0 Hz), 4.35 (1H, d, J = 11.5 Hz), 4.49-4.60 (2H, m), 4.945 (1H, d, J = 11.5 Hz), 6.90-6.96 (2H, m), 7.17-7.24 (2H, m), 7.26-7.40 (8H, m), 7.72-7.78 (2H, m). |
| 9 | Bn | H, H | N-(2-{[(3R,4R)-4-{[(4-aminophenyl)sulfonyl](benzyl)amino}pyrrolidin-3-yl]amino}ethyl)-Nα-(methoxycarbonyl)-β-phenyl-L-phenylalaninamide | (400 MHz, CD$_3$OD): 2.51-2.87 (2H, m), 2.85-2.95 (1H, m), 3.01-3.11 (1H, m), 3.40-3.50 (3H, m), 3.56 (3H, s), 3.77 (1H, dd, J = 13.0 Hz, J = 8.5 Hz), 4.00-4.10 (1H, m), 4.27 (1H, d, J = 15.5 Hz), 4.35 (1H, d, J = 11.0 Hz), 4.57 (1H, d, J = 15.5 Hz), 4.67-4.77 (1H, m), 4.91 (1H, d, J = 11.0 Hz), 6.81-6.87 (2H, m), 7.17-7.24 (2H, m), 7.25-7.39 (8H, m), 7.66-7.71 (2H, m). |

Example 10

N-{2-[{(3R,4R)-4-[[(4-aminophenyl)sulfonyl](3-methylbutyl)amino]pyrrolidin-3-yl}(methyl)amino]ethyl}-N-alpha-(methoxycarbonyl)-beta-phenyl-L-phenylalaninamide

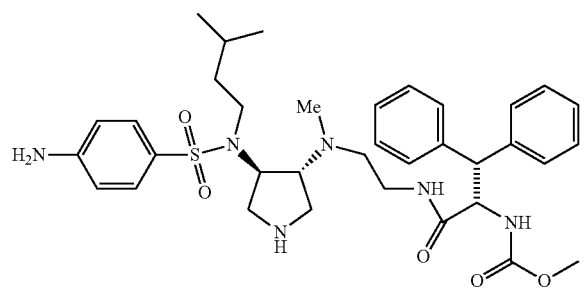 [SMILES: COC(=O)N[C@H](C(=O)NCCN(C)[C@@H]1CNC[C@H]1N(CCC(C)C)S(=O)(=O)c1ccc(N)cc1)C(c1ccccc1)c1ccccc1]

Step 1 N-(2-{[(3R,4R)-1-Benzyl-4-{(3-methylbutyl)[(4-nitrophenyl)sulfonyl]amino}pyrrolidin-3-yl](methyl)amino}ethyl)-Nα-(methoxycarbonyl)-β-phenyl-L-phenylalaninamide

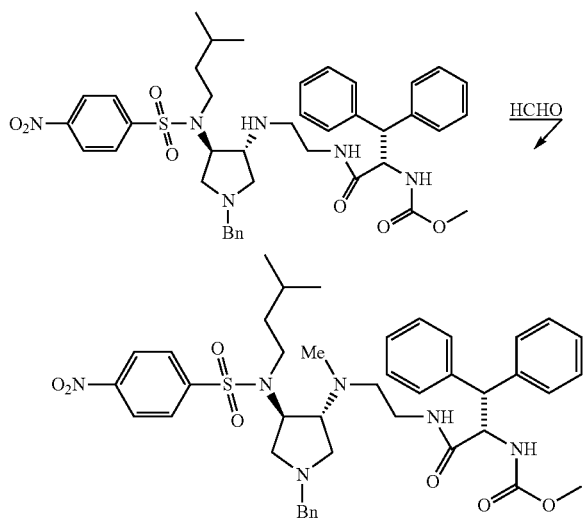

A mixture of N-(2-{[(3R,4R)-1-benzyl-4-{(3-methylbutyl)[(4-nitrophenyl)sulfonyl]amino}pyrrolidin-3-yl]amino}ethyl)-Nα-(methoxycarbonyl)-β-phenyl-L-phenylalaninamide (see Example 1, Step 12) (200 mg, 0.259 mmol) was dissolved in 20:1 MeCN—AcOH (3.5 mL) and 37% aqueous formaldehyde was added (0.68 mL) following by addition of NaBH$_3$CN (49 mg, 0.78 mmol). The mixture was stirred at ambient temperature for 3 hours and quenched with water (50 mL). The mixture was extracted with CHCl$_3$, the combined organic extracts were dried with Na$_2$SO$_4$ and evaporated. The residue was passed through silica gel layer eluting with 1% MeOH in CHCl$_3$. The solvent was evaporated giving the desired compound. LC-MS APCI: m/z 785.3 [M+H]$^+$.

Step 2 Nα-(Methoxycarbonyl)-N-(2-{methyl[(3R,4R)-4-{(3-methylbutyl)[(4-nitrophenyl) sulfonyl]amino}pyrrolidin-3-yl]amino}ethyl)-β-phenyl-L-phenylalaninamide

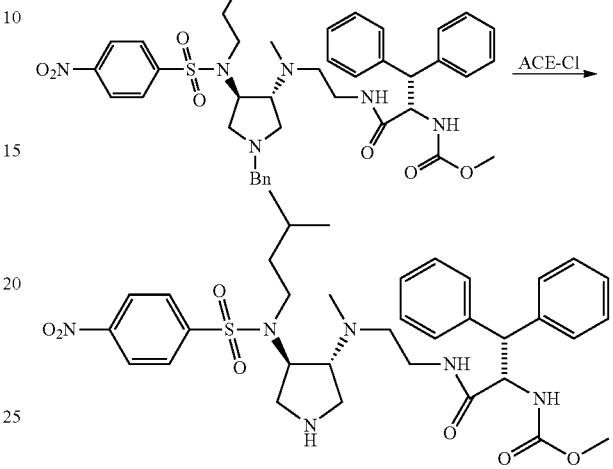

A mixture of N-(2-{[(3R,4R)-1-benzyl-4-{(3-methylbutyl)[(4-nitrophenyl)sulfonyl]amino}pyrrolidin-3-yl](methyl)amino}ethyl)-Nα-(methoxycarbonyl)-β-phenyl-L-phenylalaninamide (168 mg, 0.15 mmol), 1-chloroethyl chloroformate (72 mg, 0.5 mmol) in 1.5 mL of 1,2-dichloroethane was stirred overnight at reflux. The solvent was evaporated, the residue was re-dissolved in MeOH and the mixture was refluxed for 1 hour. MeOH was evaporated and the residue containing compound the deprotected pyrrolidine was used for the next step without additional purification. LC-MS APCI: m/z 695.3 [M+H]$^+$.

Step 3 N-{2-[{(3R,4R)-4-[[(4-aminophenyl)sulfonyl](3-methylbutyl)amino]pyrrolidin-3-yl}(methyl)amino]ethyl}-N-alpha-(methoxycarbonyl)-beta-phenyl-L-phenyl alaninamide To a mixture of Nα-(methoxycarbonyl)-N-(2-{methyl[(3R,4R)-4-{(3-methylbutyl)[(4-nitrophenyl) sulfonyl]amino}pyrrolidin-3-yl]amino}ethyl)-β-phenyl-L-phenylalaninamide (69.5 mg, 0.1 mmol), anhydrous SnCl$_2$ (95 mg, 0.5 mmol) in EtOAc, 1 mL of H$_2$O was added and the mixture was stirred at reflux for 3 hours. Saturated aqueous NaHCO$_3$ was added, and the mixture was extracted with EtOAc. The combined organic extracts were dried with Na$_2$SO$_4$ and evaporated. The residue was purified by preparative RP-HPLC. The collected fractions were evaporated, basified and extracted with CH$_2$Cl$_2$. The combined organic extracts were dried with Na$_2$SO$_4$ and evaporated. The residue was re-dissolved in 0.5 mL CH$_2$Cl$_2$ and 1-2 mL of 2N HCl in Et$_2$O was added. The mixture was diluted with Et$_2$O, the pellet was filtered off, washed with Et$_2$O and dried in vacuo. $^1$H NMR (400 MHz, CD$_3$OD): 0.925 and 0.945 (6H, two d, J=6.0 Hz), 1.50-1.67 (3H, m), 2.91 (3H, s), 3.07-3.30 (5H, m), 3.30-3.50 (3H, m), 3.52-3.60 (1H, m), 3.57 (3H, s), 3.84 (1H, dd, J=13.0 Hz, J=8.5 Hz), 4.27-4.36 (1H, m), 4.36 (1H, d, J=11.0 Hz), 4.98 (1H, d, J=11.0 Hz), 4.94-5.02 (1H, m), 6.93-6.98 (2H, m), 7.17-7.24 (2H, m), 7.26-7.39 (8H, m), 7.69-7.75 (2H, m). LC-MS APCI: m/z 665.3 [M+H]$^+$.

Example 11

N-[2-({(3R,4R)-4-[{[4-(hydroxymethyl)phenyl]sulfonyl}(3-methylbutyl)amino]pyrrolidin-3-yl}amino)ethyl]-Nalpha-(methoxycarbonyl)-beta-phenyl-L-phenylalaninamide

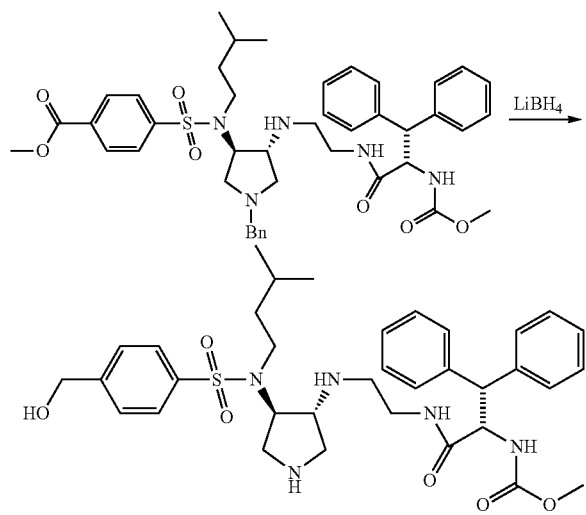

A solution containing 69 mg (0.1 mmol) of the ester substrate shown above (prepared as described in Example 1, except methyl 4-chlorosulfonylbenzoate was employed in place of 4-nitrobenzenesulfonyl chloride) dissolved in 1 mL of THF was treated with 2M LiBH$_4$ (1 eq) at room temperature for 8 hours. The mixture was quenched with H$_2$O, extracted with EtOAc, the combined extracts were dried with Na$_2$SO$_4$ and evaporated giving the crude alcohol which was purified by preparative RP-HPLC to afford the title compound. $^1$H NMR (400 MHz, CD$_3$OD): 0.92 (2×d, 2×3H, J=6.3 Hz), 1.48-1.61 (m, 3H), 2.06-2.09 (m, 2H), 3.16-3.20 (m, 1H), 3.22-3.28 (m, 2H), 3.42-3.50 (m, 2H), 3.57 (s, 3H), 3.80-3.85 (m, 1H), 4.11-4.14 (m, 1H), 4.34 (d, 1H, J=11.2 Hz), 4.73 (s, 3H), 4.91 (d, 1H, J=11.2 Hz), 7.19-7.22 (m, 2H), 7.27-7.37 (m, 8H), 7.64 (d, 2H, J=8.3 Hz), 7.93 (d, 2H, J=8.3 Hz). LC-MS APCI: m/z 666.1 [M+H]$^+$.

Example 12

N-{3-[(3R*,4S*)-4-{[(4-aminophenyl)sulfonyl](3-methylbutyl)amino}pyrrolidin-3-yl]propyl}-Nα-(methoxycarbonyl)-β-phenyl-L-phenylalaninamide

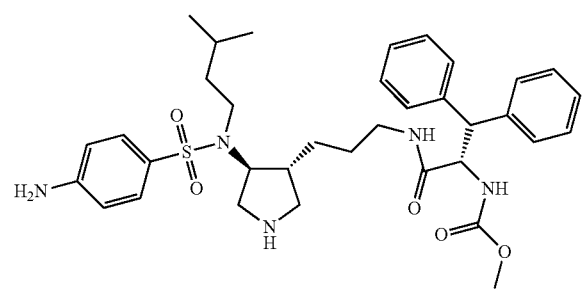 [SMILES: COC(=O)N[C@H](C(=O)NCCC[C@@H]1CNC[C@H]1N(CCC(C)C)S(=O)(=O)c1ccc(N)cc1)C(c1ccccc1)c1ccccc1]

Step 1 Benzyl (3S*,4R*)-1-(tert-butoxycarbonyl)-4-(ethoxycarbonyl)pyrrolidin-3-ylcarbamate

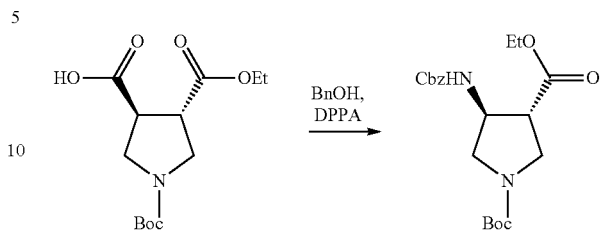

A mixture of (3S*,4S*)-1-(tert-butoxycarbonyl)-4-(ethoxycarbonyl)pyrrolidine-3-carboxylic acid (see Example 12, Step 2) (7.01 g, 24.4 mmol), benzyl alcohol (3.16 g, 29.15 mmol), diphenylphosphoryl azide (8.06 g, 29.3 mmol) and DIPEA (3.76 g, 29.15 mmol) in toluene (320 mL) was stirred at 80° C. for 15 hours. The toluene was partially evaporated, water was added and the mixture was extracted with CHCl$_3$. The combined organic extracts were dried with Na$_2$SO$_4$ and evaporated. The residue was purified by column chromatography on silica gel eluting with 5→15% MeOH in CHCl$_3$ giving the title product.

Step 2 Benzyl (3S*,4R*)-1-(tert-butoxycarbonyl)-4-formylpyrrolidin-3-ylcarbamate

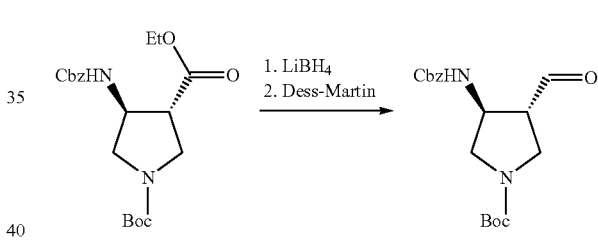

To a solution of benzyl (3S*,4R*)-1-(tert-butoxycarbonyl)-4-(ethoxycarbonyl)pyrrolidin-3-ylcarbamate (4.4 g, 11.2 mmol) in 150 mL THF, LiBH$_4$ (0.74 g, 33.6 mmol) was added and the mixture was stirred at 80° C. for 1.5 hours. The mixture was quenched with H$_2$O, extracted with EtOAc, the combined organic extracts were dried with Na$_2$SO$_4$ and evaporated. The residue was re-dissolved in 300 mL CH$_2$Cl$_2$, activated MnO$_2$ (3.86 g, 56 mmol) was added and the mixture was stirred for 24 hours at room temperature. MnO$_2$ was filtered off through Celite, and the filtrate was evaporated giving the title aldehyde.

Step 3 Benzyl (3S*,4R*)-1-(tert-butoxycarbonyl)-4-((E)-2-(methoxycarbonyl)vinyl)pyrrolidin-3-ylcarbamate

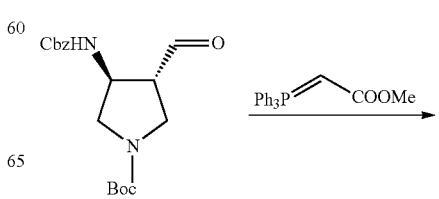

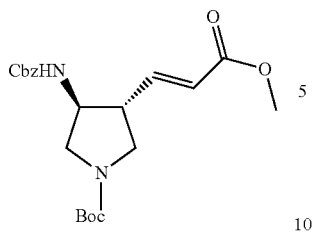

A mixture of benzyl (3S*,4R*)-1-(tert-butoxycarbonyl)-4-formylpyrrolidin-3-ylcarbamate (1.71 g, 4.9 mmol) and methyl (triphenylphosphoranilydene)acetate (1.97 g, 5.9 mmol) in 100 mL benzene was stirred at reflux for 1.5 hours. Benzene was partially evaporated and the residue was purified by column chromatography on silica gel eluting with 5→25% EtOAc in hexane to give the title compound.

Step 4 Benzyl (3S*,4R*)-1-(tert-butoxycarbonyl)-4-(3-hydroxypropyl)pyrrolidin-3-ylcarbamate

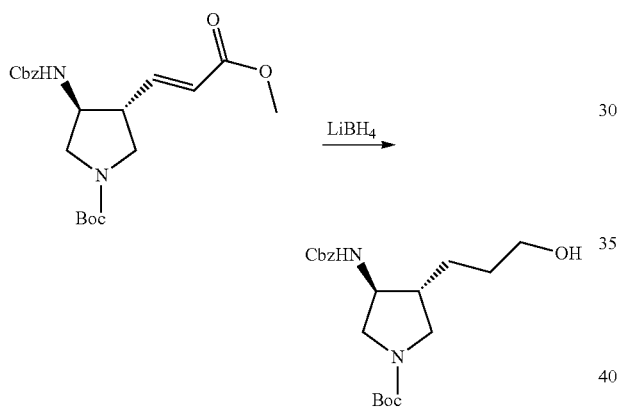

To a solution of benzyl (3S*,4R*)-1-(tert-butoxycarbonyl)-4-((E)-2-(methoxycarbonyl)vinyl)pyrrolidin-3-ylcarbamate (1.0 g, 2.47 mmol) in 100 mL THF, LiBH₄ was added (0.2 g, 9.0 mmol) and the mixture was stirred at reflux for 9 hours. The mixture was quenched with H₂O, extracted with EtOAc, the combined organic extracts were dried with Na₂SO₄ and evaporated. The residue was purified by column chromatography on silica gel eluting with 10→50% EtOAc in hexane giving the title compound.

Step 5 (3S*,4R*)-tert-Butyl 3-amino-4-(3-hydroxypropyl)pyrrolidine-1-carboxylate

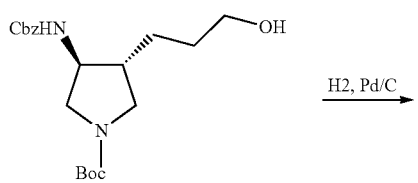

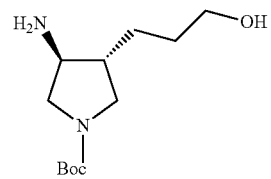

Benzyl (3S*,4R*)-1-(tert-butoxycarbonyl)-4-(3-hydroxypropyl)pyrrolidin-3-ylcarbamate (0.98 g, 2.59 mmol) was hydrogenated over 10% Pd/C (0.05 g) in MeOH for 3 hours at ambient pressure. The catalyst was filtered off and the solvent was evaporated giving the title compound.

Step 6 tert-Butyl (3R,4S)-3-(3-hydroxypropyl)-4-{[(4-nitrophenyl)sulfonyl]amino}pyrrolidine-1-carboxylate

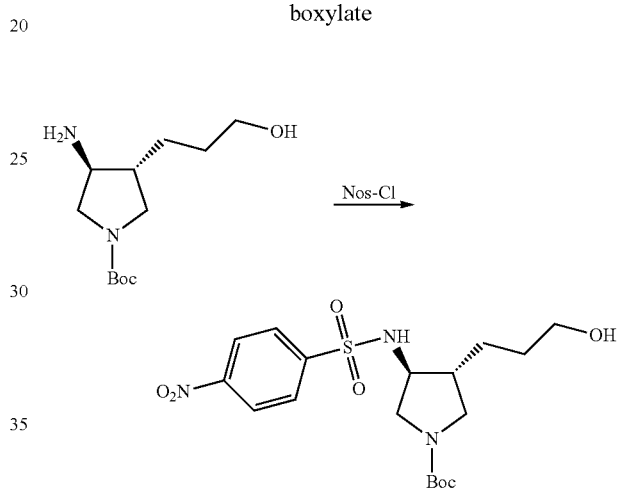

A mixture of (3S*,4R*)-tert-butyl 3-amino-4-(3-hydroxypropyl)pyrrolidine-1-carboxylate (0.55 g, 2.25 mmol) and p-nitrophenylsulfonyl chloride (0.50 g, 2.25 mmol) and Na₂CO₃ (0.29 g, 2.70 mmol) in 8 mL THF-water, 3:1, was stirred overnight at room temperature. THF was evaporated, the mixture was diluted with H₂O, extracted with CH₂Cl₂, the combined organic extracts were dried with Na₂SO₄ and evaporated. The residue was purified by column chromatography on silica gel eluting with 1→5% MeOH in CH₂Cl₂ giving the title compound.

Step 7 tert-Butyl (3R*,4S*)-3-(3-hydroxypropyl)-4-{(3-methylbutyl)[(4-nitrophenyl)sulfonyl]amino}pyrrolidine-1-carboxylate

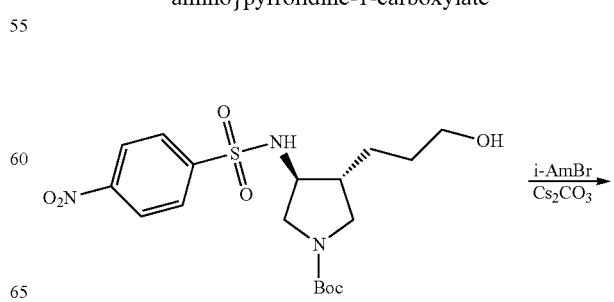

-continued

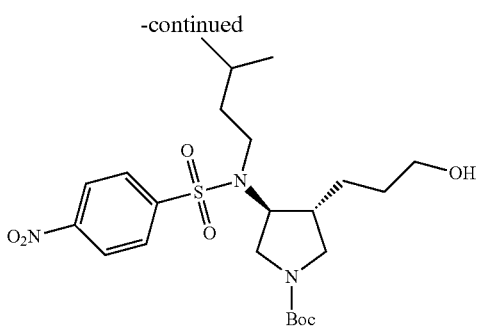

To a mixture of tert-butyl (3R*,4S*)-3-(3-hydroxypropyl)-4-{[(4-nitrophenyl)sulfonyl]amino}pyrrolidine-1-carboxylate (0.82 g, 1.91 mmol) and 1-bromo-3-methylbutane (0.30 g, 2.0 mmol) in 8 mL DMF, $Cs_2CO_3$ (0.93 g, 2.86 mmol) was added and the mixture was stirred at 3.5 hours at 85° C. The mixture was diluted with $H_2O$, extracted with $CH_2Cl_2$, the combined organic extracts were dried with $Na_2SO_4$ and evaporated. The residue was purified by column chromatography on silica gel eluting with 1→5% MeOH in $CH_2Cl_2$ giving the title compound.

Step 8 tert-Butyl (3R*,4S*)-3-(3-azidopropyl)-4-{(3-methylbutyl)[(4-nitrophenyl)sulfonyl]amino}pyrrolidine-1-carboxylate

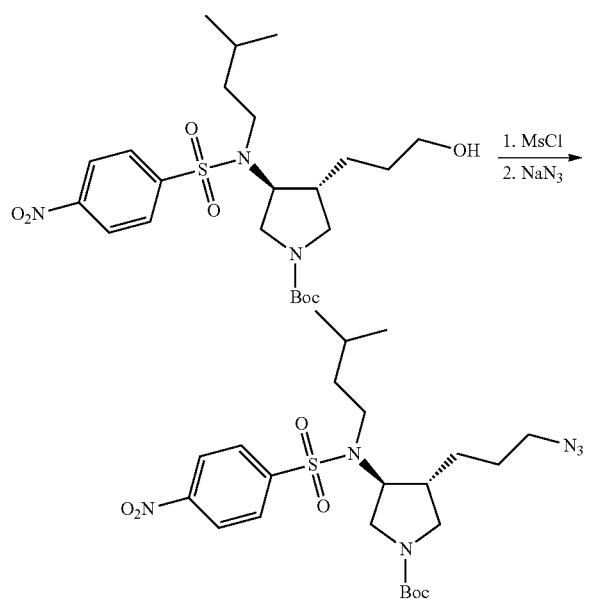

To a solution of tert-butyl (3R*,4S*)-3-(3-hydroxypropyl)-4-{(3-methylbutyl)[(4-nitrophenyl)sulfonyl]amino}pyrrolidine-1-carboxylate (0.88 g, 1.76 mmol) and $Et_3N$ (0.27 g, 2.64 mmol) in 15 mL $CH_2Cl_2$, MsCl (0.24 g, 2.11 mmol) was added dropwise in 5 mL $CH_2Cl_2$ at room temperature. The mixture was stirred for 3 hours at room temperature and poured into saturated $NH_4Cl$. The organic phase was separated and the aqueous phase was extracted with $CH_2Cl_2$. The combined organic extracts were dried with $Na_2SO_4$ and evaporated. The residue was re-dissolved in 2 mL DMSO, sodium azide was added (180 mg, 2.76 mmol) and the mixture was stirred at room temperature for 1 hour.

The mixture was diluted with $H_2O$, extracted with $CH_2Cl_2$, the combined organic extracts were dried with $Na_2SO_4$ and evaporated. The residue was purified by column chromatography on silica gel eluting with 1→5% MeOH in $CH_2Cl_2$ giving the title compound.

Step 9 tert-Butyl (3R*,4S*)-3-(3-aminopropyl)-4-{(3-methylbutyl)[(4-nitrophenyl)sulfonyl]amino}pyrrolidine-1-carboxylate To a solution of tert-butyl (3R*,4S*)-3-(3-azidopropyl)-4-{(3-methylbutyl)[(4-nitrophenyl)sulfonyl]amino}pyrrolidine-1-carboxylate (0.55 g, 1.05 mmol) in toluene (50 mL), $PPh_3$ (0.28 g, 1.05 mmol) was added and the mixture was heated at reflux for 1.5 hours. The mixture was diluted with 10 mL THF, $H_2O$ was added (28 mg, 1.57 mmol) and the reaction was heated at reflux for additional 1.5 hours. The solvents were evaporated and the residue was purified by column chromatography on silica gel eluting with 5→10% MeOH in $CH_2Cl_2$ giving the title compound.

Step 10 N-{3-[(3R*,4S*)-4-{[(4-aminophenyl)sulfonyl](3-methylbutyl)amino}pyrrolidin-3-yl]propyl}-Nα-(methoxycarbonyl)-β-phenyl-L-phenylalaninamide

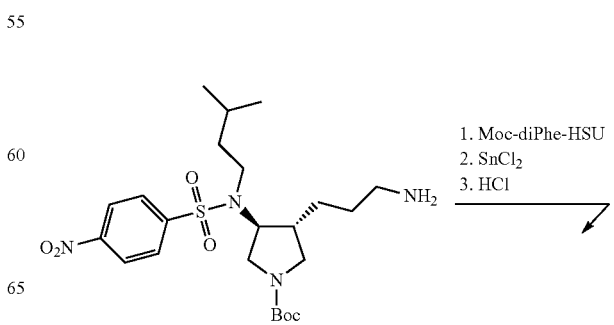

-continued

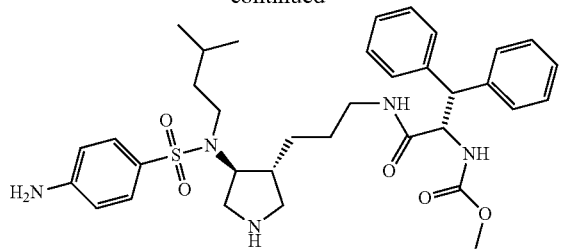

A mixture of tert-butyl (3R*,4S*)-3-(3-aminopropyl)-4-{(3-methylbutyl)[(4-nitrophenyl)sulfonyl]amino}pyrrolidine-1-carboxylate (390 mg, 0.78 mmol), saturated aqueous $NaHCO_3$ (0.5 mL), and Moc-diPhe-HSu (310 mg, 0.789 mmol) in acetone-THF, 1:1, was stirred 2 hours at room temperature. The mixture was quenched with water, and the product was extracted with $CHCl_3$. The combined organic extracts were dried with $Na_2SO_4$ and evaporated. The residue was re-dissolved in 5 mL EtOAc, anhydrous $SnCl_2$ (321 mg, 1.70 mmol) and $H_2O$ (61 μl, 3.40 mmol) were added and the mixture was stirred at reflux for 2 hours. Saturated aqueous $NaHCO_3$ was added following by addition of water, the mixture was extracted with EtOAc, the combined organic extracts were dried with $Na_2SO_4$ and evaporated. The residue was purified by column chromatography on silica gel eluting with 10-15% MeOH in $CHCl_3$. The collected fractions were evaporated, re-dissolved in 0.5 mL $CH_2Cl_2$ and 1-2 mL of 2N HCl in $Et_2O$ was added. The mixture was diluted with $Et_2O$, the pellet was filtered off, washed with $Et_2O$ and dried in vacuo at 50-60° C. giving 58 mgs of the target compound as the HCl salt. $^1H$ NMR (400 MHz, $CD_3OD$): 0.89-0.92 (m, 1H), 0.94 (dd, 3H, $J_1$=2.0 Hz, $J_2$=6.3 Hz), 1.03-1.09 (m, 3H), 1.37-1.41 (m, 1H), 1.58-1.62 (m, 2H), 2.17-2.21 (m, 1H), 2.68-2.84 (m, 3H), 3.03-3.08 (m, 2H), 3.28-3.31 (m, 2H), 3.39-3.44 (m, 1H), 3.55 (s, 3H), 3.97-4.00 (m, 1H), 4.30 (d, 1H, J=11.7 Hz), 4.88 (d, 1H, J=Hz), 7.16-7.21 (4H, m), 7.25-7.36 (m, 8H), 7.75-7.78 (m, 2H).

LC-MS APCI: m/z 651.1 $[M+H]^+$.

Assay Example 1

Assay for Inhibition of Microbial Expressed HIV Protease

Inhibition studies of the reaction of the protease (which was expressed in *Eschericia coli*) with a peptide substrate [Val-Ser-Gln-Asn-(betanapthyl)Ala-Pro-Ile-Val] (SEQ ID NO: 1). The inhibitor is first preincubated with the enzyme in assay buffer (50 mM sodium acetate, pH 5.5, 100 mM NaCl, and 0.1% BSA) for 30 minutes at room temperature. Substrate is added to 440 micromolar in a total volume of 80 microliters containing 5 picomolar HIV-1 protease, and the reaction is incubated for 1 hour at 30° C. The reaction is quenched by addition of 120 microliters of 10% phosphoric acid, and product formation is determined after separation of product and substrate on a Vydac C18 column connected to an Alliance high performance liquid chromatography system (Waters Corporation). The extent of inhibition of the reaction is determined from the peak area of the products. HPLC of the products, independently synthesized, proved quantitation standards and confirmation of the product composition. Representative compounds of the present invention exhibit inhibition of HIV-1 protease in this assay. For example, as shown by their $IC_{50}$ values in Table B below, the compounds set forth in the foregoing Examples exhibit inhibition against the wild-type HIV-1 protease enzyme.

Assay Example 2

Assay for Inhibition of HIV Replication

Assays for the inhibition of acute HIV infection of T-lymphoid cells were conducted in accordance with Vacca, J. P. et al., *Proc. Natl. Acad. Sci. USA* 1994, 91: 4096. Representative compounds of the present invention exhibit inhibition of HIV replication in this assay (also referred to herein as the "Spread Assay"). For example, as shown by their $IC_{95}$ values in Table B below, the compounds set forth in the foregoing Examples were tested in this assay and found to exhibit inhibition of HIV-1 replication.

Assay Example 3

Cytotoxicity

Cytotoxicity was determined by microscopic examination of the cells in each well in the spread assay, wherein a trained analyst observed each culture for any of the following morphological changes as compared to the control cultures: pH imbalance, cell abnormality, cytostatic, cytopathic, or crystallization (i.e., the compound is not soluble or forms crystals in the well). The toxicity value assigned to a given compound is the lowest concentration of the compound at which one of the above changes is observed. Representative compounds of the present invention do not exhibit cytotoxicity. For example, all of the exemplified compounds were tested in this assay and none was found to exhibit cytotoxicity.

TABLE B

| Example No.[1] | Enzyme Inhibition - $IC_{50}$ (nM) | Spread[2] - $IC_{95}$ (nM) |
| --- | --- | --- |
| 1 | 0.7 | 495 |
| 2 | 0.055 | 423 |
| 3 | 0.22 | 472 |
| 4 | 3.6 | 399 |
| 5 | 3.2 | 405 |
| 6 | 0.05 | 291 |
| 7 | 3.7 | 500 |
| 8 | 22 | 26% @ 500 |
| 9 | 8.6 | 505 |
| 10 | 15 | 217 |
| 11 | 0.29 | 328 |
| 12 | 0.05 | 324 |

[1]No cytotoxicity was observed for any of these compounds in the cytotoxicity assay set forth in Assay Example 3 up to a concentration of 10 μM.
[2]Conducted using 10% FBS.

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entireties into the disclosure.

What is claimed is:

1. A compound of Formula I:

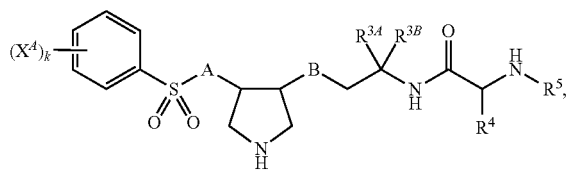

or a pharmaceutically acceptable salt thereof, wherein:

A is N—$R^1$ or CH—$R^1$;
B is N—$R^2$ or CH—$R^2$;
$R^1$ is H, $C_{1-6}$ alkyl, $C_{1-6}$ fluoroalkyl, $C_{3-6}$ cycloalkyl, $C_{1-6}$ alkyl substituted with $C_{3-6}$ cycloalkyl, or $C_{1-6}$ alkyl substituted with AryA;
$R^2$ is H, $C_{1-6}$ alkyl, $C_{1-6}$ fluoroalkyl, $C_{3-6}$ cycloalkyl, $C_{1-6}$ alkyl substituted with $C_{3-6}$ cycloalkyl, $C_{1-6}$ alkyl substituted with AryB, C(O)—$C_{1-6}$ alkyl, or $SO_2$—$C_{1-6}$ alkyl;
$R^{3A}$ is H, $C_{1-6}$ alkyl, $C_{1-6}$ fluoroalkyl, $C_{3-5}$ cycloalkyl, or $C_{1-6}$ alkyl substituted with $C_{3-5}$ cycloalkyl;
$R^{3B}$ is H or $C_{1-6}$ alkyl;
each $X^A$ is independently:
  (1) $C_{1-6}$ alkyl,
  (2) $C_{3-6}$ cycloalkyl,
  (3) $C_{1-6}$ haloalkyl,
  (4) OH,
  (5) O—$C_{1-6}$ alkyl,
  (6) O—$C_{1-6}$ haloalkyl,
  (7) O—$C_{3-6}$ cycloalkyl,
  (8) SH,
  (9) S—$C_{1-6}$ alkyl,
  (10) S—$C_{1-6}$ haloalkyl,
  (11) S—$C_{3-6}$ cycloalkyl,
  (12) halo,
  (13) CN,
  (14) $NO_2$,
  (15) $NH_2$,
  (16) N(H)—$C_{1-6}$ alkyl,
  (17) N(—$C_{1-6}$ alkyl)$_2$,
  (18) N(H)C(O)—$C_{1-6}$ alkyl,
  (19) N(H)CH(O),
  (20) CH(O),
  (21) C(O)—$C_{1-6}$ alkyl,
  (22) C(O)OH,
  (23) C(O)O—$C_{1-6}$ alkyl,
  (24) $SO_2H$,
  (25) $SO_2$—$C_{1-6}$ alkyl, or
  (26) $C_{1-6}$ alkyl substituted with:
    (a) $C_{3-6}$ cycloalkyl,
    (b) $C_{1-6}$ haloalkyl,
    (c) OH,
    (d) O—$C_{1-6}$ alkyl,
    (e) O—$C_{1-6}$ haloalkyl,
    (f) O—$C_{3-6}$ cycloalkyl,
    (g) SH,
    (h) S—$C_{1-6}$ alkyl,
    (i) S—$C_{1-6}$ haloalkyl,
    (j) S—$C_{3-6}$ cycloalkyl,
    (k) halo,
    (l) CN,
    (m) $NO_2$,
    (n) $NH_2$,
    (o) N(H)—$C_{1-6}$ alkyl,
    (p) N(—$C_{1-6}$ alkyl)$_2$,
    (q) N(H)C(O)—$C_{1-6}$ alkyl,
    (r) N(H)CH(O),
    (s) CH(O),
    (t) C(O)—$C_{1-6}$ alkyl,
    (u) C(O)OH,
    (v) C(O)O—$C_{1-6}$ alkyl,
    (w) $SO_2H$, or
    (x) $SO_2$—$C_{1-6}$ alkyl;
k is an integer equal to 0, 1, 2, or 3;
$R^4$ is:

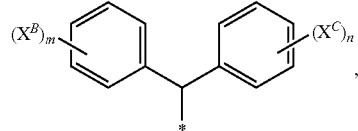

wherein the asterisk (*) denotes the point of attachment to the rest of the compound;
each $X^B$ and each $X^C$ are independently selected from the group consisting of:
  (1) $C_{1-3}$ alkyl,
  (2) cyclopropyl,
  (3) $CF_3$,
  (4) OH, (5) O—C$_{1-3}$ alkyl,
(6) OCF$_3$,
(7) Cl,
(8) Br,
(9) F,
(10) CN,
(11) NO$_2$,
(12) NH$_2$,
(13) N(H)—C$_{1-3}$ alkyl,
(14) N(—C$_{1-3}$ alkyl)$_2$,
(15) C(O)—C$_{1-3}$ alkyl,
(16) CO$_2$H,
(17) C(O)O—C$_{1-3}$ alkyl,
(18) CH$_2$OH, and
(19) CH$_2$O—C$_{1-3}$ alkyl;

m is an integer equal to 0, 1, 2, or 3;
n is an integer equal to 0, 1, 2, or 3;
R$^5$ is H, C$_{1-6}$ alkyl, C$_{3-6}$ cycloalkyl, C$_{1-6}$ alkyl substituted with C$_{3-6}$ cycloalkyl, or C(O)—R$^K$;
R$^K$ is:
  (1) C$_{1-6}$ alkyl,
  (2) C$_{3-6}$ cycloalkyl,
  (3) C$_{1-6}$ alkyl substituted with C$_{3-6}$ cycloalkyl,
  (4) O—C$_{1-6}$ alkyl,
  (5) O—C$_{1-6}$ alkyl substituted with O—C$_{1-6}$ alkyl,
  (6) O—C$_{1-6}$ fluoroalkyl,
  (7) C(O)O—C$_{1-6}$ alkyl,
  (8) C$_{1-6}$ alkyl substituted with C(O)O—C$_{1-6}$ alkyl,
  (9) C$_{1-6}$ alkyl substituted with C(O)OH,
  (10) C$_{1-6}$ alkyl substituted with C(O)—C$_{1-6}$ alkyl,
  (11) N(H)—C$_{1-6}$ alkyl,
  (12) N(—C$_{1-6}$ alkyl)$_2$,
  (13) C$_{1-6}$ alkyl substituted with NH$_2$, N(H)—C$_{1-6}$ alkyl, or N(—C$_{1-6}$ alkyl)$_2$,
  (14) AryC,
  (15) C$_{1-6}$ alkyl substituted with AryC,
  (16) O—C$_{1-6}$ alkyl substituted with AryC,
  (17) HetA,
  (18) C$_{1-6}$ alkyl substituted with HetA,
  (19) O—C$_{1-6}$ alkyl substituted with HetA,
  (20) HetB, or
  (21) O-HetB;

AryA is an aryl which is independently phenyl or naphthyl, wherein the phenyl or naphthyl is optionally substituted with from 1 to 4 Y$^A$ wherein each Y$^A$ independently has the same definition as X$^B$;
AryB is an aryl which is independently phenyl or naphthyl, wherein the phenyl or naphthyl is optionally substituted with from 1 to 4 Y$^A$ wherein each Y$^A$ independently has the same definition as X$^B$;
AryC is an aryl which is independently phenyl or naphthyl, wherein the phenyl or naphthyl is optionally substituted with from 1 to 4 Y$^B$ wherein each Y$^B$ independently has the same definition as X$^B$;
HetA is a heteroaryl which is independently (i) a 5- or 6-membered heteroaromatic ring containing from 1 to 4 heteroatoms independently selected from N, O and S, or (ii) is a heterobicyclic ring selected from quinolinyl, isoquinolinyl, and quinoxalinyl; wherein the heteroaromatic ring (i) or the bicyclic ring (ii) is optionally substituted with from 1 to 4 Y$^C$ wherein each Y$^C$ independently has the same definition as X$^B$; and
HetB is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or S(O)$_2$, and wherein the saturated or unsaturated heterocyclic ring is optionally substituted with from 1 to 4 substituents each of which is independently halogen, CN, C$_{1-6}$ alkyl, OH, oxo, O—C$_{1-6}$ alkyl, C$_{1-6}$ haloalkyl, O—C$_{1-6}$ haloalkyl, C(O)NH$_2$, C(O)N(H)—C$_{1-6}$ alkyl, C(O)N(—C$_{1-6}$ alkyl)$_2$, C(O)H, C(O)—C$_{1-6}$ alkyl, CO$_2$H, CO$_2$—C$_{1-6}$ alkyl, SO$_2$H, or SO$_2$—C$_{1-6}$ alkyl.

2. The compound according to claim 1, or a pharmaceutically acceptable salt thereof, wherein
R$^1$ is C$_{1-6}$ alkyl or C$_{1-6}$ alkyl substituted with AryA;
R$^2$ is H, C$_{1-6}$ alkyl, C$_{1-6}$ alkyl substituted with AryB, C(O)—C$_{1-6}$ alkyl, or SO$_2$—C$_{1-6}$ alkyl;
R$^{3A}$ is H or C$_{1-6}$ alkyl;
R$^{3B}$ is H or C$_{1-6}$ alkyl;
R$^4$ is:

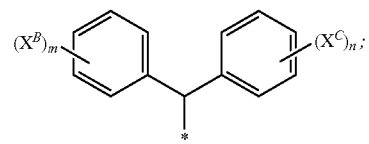

each X$^B$ and each X$^C$ are independently selected from the group consisting of:
(1) C$_{1-3}$ alkyl,
(2) cyclopropyl,
(3) CF$_3$,
(4) OH,
(5) O—C$_{1-3}$ alkyl,
(6) OCF$_3$,
(7) Cl,
(8) Br,
(9) F,
(10) CN,
(11) NO$_2$,
(12) NH$_2$,
(13) N(H)—C$_{1-3}$ alkyl,
(14) N(—C$_{1-3}$ alkyl)$_2$,
(15) C(O)—C$_{1-3}$ alkyl,
(16) CO$_2$H,
(17) C(O)O—C$_{1-3}$ alkyl,
(18) CH$_2$OH, and
(19) CH$_2$O—C$_{1-3}$ alkyl;

m is an integer equal to 0, 1, or 2;
n is an integer equal to 0, 1, or 2;
each X$^A$ is independently:
(1) C$_{1-3}$ alkyl,
(2) cyclopropyl,
(3) CF$_3$,
(4) OH,
(5) O—C$_{1-3}$ alkyl,
(6) OCF$_3$,
(7) Cl,
(8) Br,
(9) F,
(10) CN,
(11) NO$_2$,
(12) NH$_2$,
(13) N(H)—C$_{1-3}$ alkyl,
(14) N(—C$_{1-3}$ alkyl)$_2$,
(15) C(O)—C$_{1-3}$ alkyl,
(16) CO$_2$H,
(17) C(O)O—C$_{1-3}$ alkyl, or

(18) C_{1-3} alkyl substituted with
  (a) cyclopropyl,
  (b) CF_3,
  (c) OH,
  (d) O—C_{1-3} alkyl,
  (e) OCF_3,
  (f) Cl,
  (g) Br,
  (h) F,
  (i) CN,
  (j) NO_2,
  (k) NH_2,
  (l) N(H)—C_{1-3} alkyl,
  (m) N(—C_{1-3} alkyl)_2,
  (n) C(O)—C_{1-3} alkyl,
  (o) CO_2H, or
  (p) C(O)O—C_{1-3} alkyl;
k is an integer equal to 0, 1, or 2;
R^5 is H, C_{1-6} alkyl, C(O)—C_{1-6} alkyl, C(O)O—C_{1-6} alkyl, C(O)N(—C_{1-6} alkyl)_2, C(O)—HetA, C(O)OCH_2-HetA, C(O)-HetB, or C(O)O-HetB;
AryA is phenyl which is optionally substituted with from 1 to 3 substituents each of which is independently C_{1-3} alkyl, CF_3, OH, O—C_{1-3} alkyl, OCF_3, Cl, Br, F, CN, NH_2, N(H)—C_{1-3} alkyl, N(—C_{1-3} alkyl)_2, C(O)—C_{1-3} alkyl, CO_2H, C(O)O—C_{1-3} alkyl, CH_2OH, CH_2O—C_{1-3} alkyl, C(O)—C_{1-3} alkyl, or SO_2—C_{1-3} alkyl;
HetA is a heteroaryl selected from the group consisting of pyrrolyl, imidazolyl, pyridyl, pyrazinyl, quinolyl, isoquinolyl, and quinoxalinyl, wherein the heteroaryl is optionally substituted with from 1 to 3 substituents each of which is independently C_{1-3} alkyl, CF_3, OH, O—C_{1-3} alkyl, OCF_3, Cl, Br, F, CN, NH_2, N(H)—C_{1-3} alkyl, N(C_{1-3} alkyl)_2, C(O)—C_{1-3} alkyl, CO_2—C_{1-3} alkyl, or SO_2—C_{1-3} alkyl; and
HetB is a saturated heterocyclic ring selected from the group consisting of tetrahydrofuranyl, pyrrolidinyl, piperidinyl, piperazinyl, morpholinyl, and thiomorpholinyl in which the S is optionally oxidized to S(O) or S(O)_2, and wherein the ring is optionally substituted with 1 or 2 substituents each of which is independently C_{1-3} alkyl, oxo, C(O)N(C_{1-3} alkyl)_2, C(O)—C_{1-3} alkyl, CO_2—C_{1-3} alkyl, or S(O)_2—C_{1-3} alkyl.

3. The compound according to claim 2, or a pharmaceutically acceptable salt thereof, wherein:
R^1 is CH_3, CH_2CH_3, CH(CH_3)_2, CH_2CH_2CH_3, CH_2CH(CH_3)_2, CH_2CH_2CH(CH_3)_2, or CH_2CH_2CH_2CH(CH_3)_2;
R^2 is H or CH_3;
R^{3A} is H, CH_3, CH_2CH_3, CH(CH_3)_2, CH_2CH_2CH_3, CH_2CH(CH_3)_2, C(CH_3)_3, CH_2CH_2CH(CH_3)_2, or CH_2CH_2CH_2CH(CH_3)_2;
R^{3B} is H or CH_3;
each X^B and each X^C are independently selected from the group consisting of:
  (1) CH_3,
  (2) CH_2CH_3,
  (3) CF_3,
  (4) OH,
  (5) OCH_3,
  (6) OCF_3,
  (7) Cl,
  (8) Br,
  (9) F,
  (10) CN,
  (11) NH_2,
  (12) N(H)CH_3,
  (13) N(CH_3)_2,
  (14) C(O)CH_3,
  (15) C(O)OCH_3,
  (16) CH_2OH, and
  (17) CH_2OCH_3;
each X^A is independently:
  (1) CH_3,
  (2) CH_2CH_3,
  (3) CF_3,
  (4) OH,
  (5) OCH_3,
  (6) OCF_3,
  (7) Cl,
  (8) Br,
  (9) F,
  (10) CN,
  (11) NH_2,
  (12) N(H)CH_3,
  (13) N(CH_3)_2,
  (14) C(O)CH_3,
  (15) C(O)OCH_3,
  (16) CH_2OH,
  (17) CH_2OCH_3,
  (18) CH_2NH_2,
  (19) CH_2N(H)CH_3,
  (20) CH_2N(CH_3)_2,
  (21) CH(CH_3)OH,
  (22) CH(CH_3)OCH_3,
  (23) CH(CH_3)NH_2,
  (24) CH(CH_3)N(H)CH_3, or
  (25) CH(CH_3)N(CH_3)_2;
R^5 is H, CH_3, C(O)CH_3, C(O)OCH_3, C(O)OC(CH_3)_3, C(O)N(CH_3)_2, C(O)-morpholinyl, C(O)-pyridyl, or C(O)O—CH_2-pyridyl.

4. The compound according to claim 3, or a pharmaceutically acceptable salt thereof, wherein:
R^4 is:

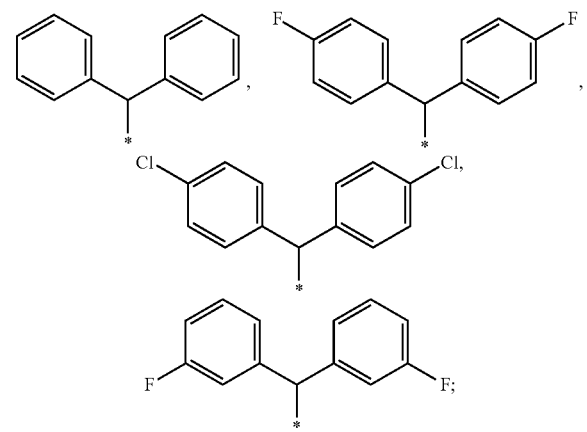

there are 1 or 2 X^A groups on the phenylsulfonyl moiety wherein one X^A is in the para position on the phenyl ring and is CH_3, Cl, Br, F, NH_2, CH_2NH_2, C(O)CH_3, CH_2OH, or CH(CH_3)OH; and the other, optional X^A is in the meta position on the phenyl ring and is Cl, Br, or F;
R^5 is H, CH_3, C(O)OCH_3, C(O)OC(CH_3)_3, or C(O)O—CH_2-pyridyl.

5. The compound according to any one of claims 1 to 4, which is a compound of Formula II:

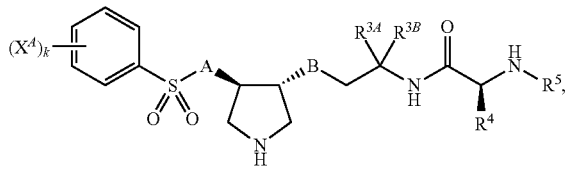

(II)

or a pharmaceutically acceptable salt thereof.

6. The compound according to claim 1, or a pharmaceutically acceptable salt thereof, wherein:
A is N—$R^1$;
B is N—$R^2$;
$R^1$ is $C_{3-6}$ alkyl or $CH_2$-AryA;
$R^2$ is H or $C_{1-6}$ alkyl;
$R^{3A}$ is H or $C_{1-6}$ alkyl;
$R^{3B}$ is H or $C_{1-6}$ alkyl;
m is an integer equal to 0, 1, or 2;
n is an integer equal to 0, 1, or 2;
each $X^A$ is independently:
 (1) $C_{1-3}$ alkyl,
 (2) cyclopropyl,
 (3) $CF_3$,
 (4) OH,
 (5) O—$C_{1-3}$ alkyl,
 (6) $OCF_3$,
 (7) Cl,
 (8) Br,
 (9) F,
 (10) CN,
 (11) $NO_2$,
 (12) $NH_2$,
 (13) N(H)—$C_{1-3}$ alkyl,
 (14) N(—$C_{1-3}$ alkyl)$_2$,
 (15) C(O)—$C_{1-3}$ alkyl,
 (16) $CO_2H$,
 (17) C(O)O—$C_{1-3}$ alkyl, or
 (18) $C_{1-3}$ alkyl substituted with
  (a) cyclopropyl,
  (b) $CF_3$,
  (c) OH,
  (d) O—$C_{1-3}$ alkyl,
  (e) $OCF_3$,
  (f) Cl,
  (g) Br,
  (h) F,
  (i) CN,
  (j) $NO_2$,
  (k) $NH_2$,
  (l) N(H)—$C_{1-3}$ alkyl,
  (m) N(—$C_{1-3}$ alkyl)$_2$,
  (n) C(O)—$C_{1-3}$ alkyl,
  (o) $CO_2H$, or
  (p) C(O)O—$C_{1-3}$ alkyl;
k is an integer equal to 0, 1, or 2;
$R^5$ is C(O)O—$C_{1-6}$ alkyl; and
AryA is phenyl which is optionally substituted with from 1 to 3 substituents each of which is independently $C_{1-3}$ alkyl, $CF_3$, OH, O—$C_{1-3}$ alkyl, $OCF_3$, Cl, Br, F, CN, $NH_2$, N(H)—$C_{1-3}$ alkyl, N(—$C_{1-3}$ alkyl)$_2$, C(O)—$C_{1-3}$ alkyl, $CO_2H$, C(O)O—$C_{1-3}$ alkyl, $CH_2OH$, $CH_2O$—$C_{1-3}$ alkyl, C(O)—$C_{1-3}$ alkyl, or $SO_2$—$C_{1-3}$ alkyl.

7. The compound according to claim 6, or a pharmaceutically acceptable salt thereof, wherein:

$R^1$ is $CH(CH_3)_2$, $CH_2CH_2CH_3$, $CH_2CH(CH_3)_2$, $CH_2CH_2CH(CH_3)_2$, $CH_2CH_2CH_2CH(CH_3)_2$, or benzyl;
$R^2$ is H or $CH_3$;
$R^{3A}$ is H, $CH_3$, $CH_2CH_3$, $CH(CH_3)_2$, $CH_2CH_2CH_3$, $CH_2CH(CH_3)_2$, $C(CH_3)_3$, $CH_2CH_2CH(CH_3)_2$, or $CH_2CH_2CH_2CH(CH_3)_2$
$R^{3B}$ is H or $CH_3$;
each $X^B$ and each $X^C$ are independently selected from the group consisting of:
 (1) $CH_3$,
 (2) $CH_2CH_3$,
 (3) $CF_3$,
 (4) OH,
 (5) $OCH_3$,
 (6) $OCF_3$,
 (7) Cl,
 (8) Br,
 (9) F,
 (10) CN,
 (11) $NH_2$,
 (12) N(H)$CH_3$,
 (13) N($CH_3$)$_2$,
 (14) C(O)$CH_3$,
 (15) C(O)O$CH_3$,
 (16) $CH_2OH$, and
 (17) $CH_2OCH_3$;
m is an integer equal to 0, 1, or 2;
n is an integer equal to 0, 1, or 2;
each $X^A$ is independently:
 (1) $CH_3$,
 (2) $CH_2CH_3$,
 (3) $CF_3$,
 (4) OH,
 (5) $OCH_3$,
 (6) $OCF_3$,
 (7) Cl,
 (8) Br,
 (9) F,
 (10) CN,
 (11) $NH_2$,
 (12) N(H)$CH_3$,
 (13) N($CH_3$)$_2$,
 (14) C(O)$CH_3$,
 (15) C(O)O$CH_3$,
 (16) $CH_2OH$,
 (17) $CH_2OCH_3$,
 (18) $CH_2NH_2$,
 (19) $CH_2$N(H)$CH_3$,
 (20) $CH_2$N($CH_3$)$_2$,
 (21) CH($CH_3$)OH,
 (22) CH($CH_3$)$OCH_3$,
 (23) CH($CH_3$)$NH_2$,
 (24) CH($CH_3$)N(H)$CH_3$, or
 (25) CH($CH_3$)N($CH_3$)$_2$;
k is an integer equal to 0, 1, or 2;
$R^5$ is C(O)$OCH_3$ or C(O)OC($CH_3$)$_3$.

8. The compound according to claim 7, or a pharmaceutically acceptable salt thereof, wherein:
$R^1$ is $CH(CH_3)_2$, $CH_2CH(CH_3)_2$, $CH_2CH_2CH(CH_3)_2$, or $CH_2CH_2CH_2CH(CH_3)_2$;
either (i) $R^{3A}$ is H, $CH_3$, $CH_2CH_3$, $CH(CH_3)_2$, $CH_2CH_2CH_3$, $CH_2CH(CH_3)_2$, $C(CH_3)_3$, $CH_2CH_2CH(CH_3)_2$, or $CH_2CH_2CH_2CH(CH_3)_2$, and $R^{3B}$ is H; or (ii) $R^{3A}$ and $R^{3B}$ are both $CH_3$;

R⁴ is:

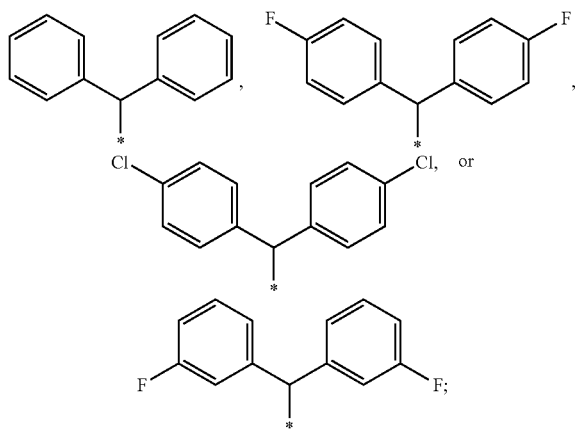

there are 1 or 2 $X^A$ groups on the phenylsulfonyl moiety wherein one $X^A$ is in the para position on the phenyl ring and is $CH_3$, Cl, Br, F, $NH_2$, $CH_2NH_2$, $C(O)CH_3$, $CH_2OH$, or $CH(CH_3)OH$; and the other, optional $X^A$ is in the meta position on the phenyl ring and is Cl, Br, or F;

R⁵ is $C(O)OCH_3$.

9. The compound according to any one of claims 6 to 8, or a pharmaceutically acceptable salt thereof, which is a compound of Formula III:

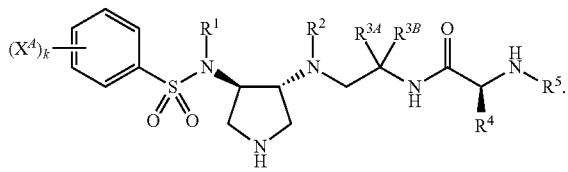

(III)

10. A compound selected from the group consisting of:
N-(2-{[(3R,4R)-4-{[(4-aminophenyl)sulfonyl](3-methylbutyl)amino}pyrrolidin-3-yl]amino}ethyl)-Nα-(methoxycarbonyl)-β-phenyl-L-phenylalaninamide;
N-[(2S)-1-{[(3R,4R)-4-{[(4-aminophenyl)sulfonyl](3-methylbutyl)amino}pyrrolidin-3-yl]amino}propan-2-yl]-Nα-(methoxycarbonyl)-β-phenyl-L-phenylalaninamide;
N-[(2S)-1-{[(3R,4R)-4-{[(4-aminophenyl)sulfonyl](3-methylbutyl)amino}pyrrolidin-3-yl]amino}butan-2-yl]-Nα-(methoxycarbonyl)-β-phenyl-L-phenylalaninamide;
N-(1-{[(3R,4R)-4-{[(4-aminophenyl)sulfonyl](3-methylbutyl)amino}pyrrolidin-3-yl]amino}hexan-2-yl)-Nα-(methoxycarbonyl)-β-phenyl-L-phenylalaninamide;
N-[(2S)-1-{[(3R,4R)-4-{[(4-aminophenyl)sulfonyl](3-methylbutyl)amino}pyrrolidin-3-yl]amino}-4-methylpentan-2-yl]-Nα-(methoxycarbonyl)-β-phenyl-L-phenylalaninamide;
N-(1-{[(3R,4R)-4-{[(4-aminophenyl)sulfonyl](3-methylbutyl)amino}pyrrolidin-3-yl]amino}-2-methylpropan-2-yl)-Nα-(methoxycarbonyl)-β-phenyl-L-phenylalaninamide;
N-(2-{[(3R,4R)-4-{[(4-aminophenyl)sulfonyl](2-methylpropyl)amino}pyrrolidin-3-yl]amino}ethyl)-Nα-(methoxycarbonyl)-β-phenyl-L-phenylalaninamide;
N-(2-{[(3R,4R)-4-{[(4-aminophenyl)sulfonyl] (propyl)amino}pyrrolidin-3-yl]amino}ethyl)-Nα-(methoxycarbonyl)-β-phenyl-L-phenylalaninamide;
N-(2-{[(3R,4R)-4-{[(4-aminophenyl)sulfonyl] (benzyl)amino}pyrrolidin-3-yl]amino}ethyl)-Nα-(methoxycarbonyl)-β-phenyl-L-phenylalaninamide;
N-{2-[{(3R,4R)-4-[[(4-aminophenyl)sulfonyl](3-methylbutyl)amino]pyrrolidin-3-yl}(methyl)amino]ethyl}-N-alpha-(methoxycarbonyl)-beta-phenyl-L-phenylalaninamide;
N-[2-({(3R,4R)-4-[{[4-(hydroxymethyl)phenyl]sulfonyl}(3-methylbutyl)amino]pyrrolidin-3-yl}amino)ethyl]-Nalpha-(methoxycarbonyl)-beta-phenyl-L-phenylalaninamide;
N-{3-[(3R*,4S*)-4-{[(4-aminophenyl)sulfonyl](3-methylbutyl)amino}pyrrolidin-3-yl]propyl}-Nα-(methoxycarbonyl)-β-phenyl-L-phenylalaninamide;
and pharmaceutically acceptable salts thereof.

11. A pharmaceutical composition comprising an effective amount of a compound according to any one of claims 1 to 10 or a pharmaceutically acceptable salt thereof, and a pharmaceutically acceptable carrier.

12. A method for the treatment of infection by HIV in a subject in need thereof, which comprises administering to the subject an effective amount of the compound according to any one of claims 1 to 10 or a pharmaceutically acceptable salt thereof.

13. A method for the treatment of infection by HIV in a subject in need thereof, which comprises administering to the subject an effective amount of the pharmaceutical composition according to claim 11.

\* \* \* \* \*